(12) United States Patent
Pain et al.

(10) Patent No.: US 11,781,191 B2
(45) Date of Patent: Oct. 10, 2023

(54) **COMPOSITIONS AND METHOD FOR DETECTING *MYCOBACTERIUM RIYADHENSE***

(71) Applicant: King Abdullah University of Science and Technology, Thuwal (SA)

(72) Inventors: Arnab Pain, Thuwal (SA); Qingtian Guan, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 318 days.

(21) Appl. No.: 16/988,617

(22) Filed: Aug. 8, 2020

(65) Prior Publication Data

US 2021/0102240 A1 Apr. 8, 2021

Related U.S. Application Data

(60) Provisional application No. 62/884,203, filed on Aug. 8, 2019.

(51) Int. Cl.
*C12Q 1/689* (2018.01)
(52) U.S. Cl.
CPC .................................... *C12Q 1/689* (2013.01)
(58) Field of Classification Search
CPC ....................................................... C12Q 1/689
USPC ......................................................... 514/29
See application file for complete search history.

(56) References Cited

FOREIGN PATENT DOCUMENTS

JP WO2014115747 * 7/2014

OTHER PUBLICATIONS

Bouw A. Master Thesis: Presence of esxA (ESAT-6) and esxB (CFP-10) by non-tuberculous mycobacterial species. Farm animal health and veterinary public health, Utrecht University, Utrecht, The Netherlands. (2020) (Year: 2020).*
Search results: 16988617-10.mg, dated on Nov. 11, 2022 in prosecution history (Year: 2022).*
Broad Institute. Picard tools, https://broadinstitute.github.io/picard/. 2016. https://broadinstitute.github.io/picard/%5Cnhttp://broadinstitute.github.io/picard/.
Abdallah, et al., "Type VII secretion—mycobacteria show the way", Nat. Rev. Microbiol., 5(11): 883-91 (2007).
Alexander, et al., "Novel *Mycobacterium tuberculosis* Complex Pathogen M. Mungi.", Emerg Infect Dis., 16(8): 1296-9 (2010).
Alikhan, et al., "BLAST Ring Image Generator (BRIG): simple prokaryote genome comparisons", BMC Genomics, 12(402): 1-10 (2011).
Alkan, et al., "Genome structural variation discovery and genotyping", Nat. Rev. Genet., 12(5): 363-76 (2011).
Althawadi, et al., "*Mycobacterium riyadhense* in Saudi Arabia", Emerging Infectious Diseases, 23(10): 1732-1734 (2017).
Baker, et al., "Composite Long- and Short-Read Sequencing Delivers a Complete Genome Sequence of B04Sm5, a Reutericyclin- and Mutanocyclin-Producing Strain of *Streptococcus mutans*", PLoS One, 9(47):1-2 (2014).
Belisle, et al., "Isolation of Genomic DNA from Myobacteria", Methods Mol Biol., 101: 31-44 (1998).
Blouin, et al., "Significance of the Identification in the Horn of Africa of an Exceptionally Deep Branching *Mycobacterium tuberculosis* Clade", PLoS One, 7(12): e52841, 15 pages (2012).
Bolger, et al., "Trimmomatic: a flexible trimmer for Illumina sequence data", Bioinformatics, 30(15): 2114-20 (2014).
Boritsch, et al., "A glimpse into the past and predictions for the future: the molecular evolution of the tuberculosis agent", Mol. Microbiol., 93(5): 835-52 (2014).
Boritsch, et al., "pks5_recombination_mediated surface remodelling in *Mycobacterium tuberculosis* emergence", Nat. Microbiol., 1:15019 (2016).
Brosch, et al., "A new evolutionary scenario for the *Mycobacterium tuberculosis* complex", Proc. Natl. Acad. Sci., 99(6): 3684-9 (2002).
Brown-Elliott, et al., "*Mycobacterium decipiens* sp. nov., a new species closely related to the *Mycobacterium tuberculosis* complex", Int. J. Syst. Evol. Microbiol., 68: 3557-62 (2018).
Camacho, et al., "BLAST+: architecture and applications", BMC Bioinformatics, 10:421,9 pages (2009).
Capella-Gutiérrez, et al., "trimAl: a tool for automated alignment trimming in large-scale phylogenetic analyses", Bioinformatics, 25(15): 1972-3 (2009).
Carbonne, et al., "Outbreak of Nontuberculous Mycobacterial Subcutaneous Infections Related to Multiple Mesotherapy Injections", J. Clin. Microbiol., 47: 1961-4 (2009).
Choi, et al., "Lung Infection Caused by *Mycobacterium riyadhense* Confused with *Mycobacterium tuberculosis*: The First Case in Korea", Ann. Lab. Med. 32: 298-303 (2012).
Cohen, et al., "The PGRS domain from PE_PGRS33 of *Mycobacterium tuberculosis* is target of humoral immune response in mice and humans", Front. Immunol., 5(236): 1-9 (2014).
Cooper, et al., "Postsegregational killing does not increase plasmid stability but acts to mediate the exclusion of competing plasmids", Proc. Natl. Acad. Sci., 97(23): 12643-8 (2000).

(Continued)

*Primary Examiner* — Yih-Horng Shiao
(74) *Attorney, Agent, or Firm* — PABST PATENT GROUP LLP

(57) ABSTRACT

Oligonucleotides for use in amplifying at least one gene present in *M. riyadhense* are disclosed. The oligoncleotides include forward primers, SEQ ID NO:1, 3, 5, and 7 and the reverse primers comprises, consists essentially of or consists of SEQ ID NO:2, 4, 6, and 8, fragment(s), derivative(s), mutation(s), or complementary sequence(s) thereof. Also provided are methods for detecting the presence of *M. riyadhense* in a sample. The method includes contacting a biological sample with a pair of forward/reverse primers, under conditions suitable for amplification of at least one gene product from *M. riyadhense* if present in a sample and detecting the presence of the amplification product.

Figure 1:
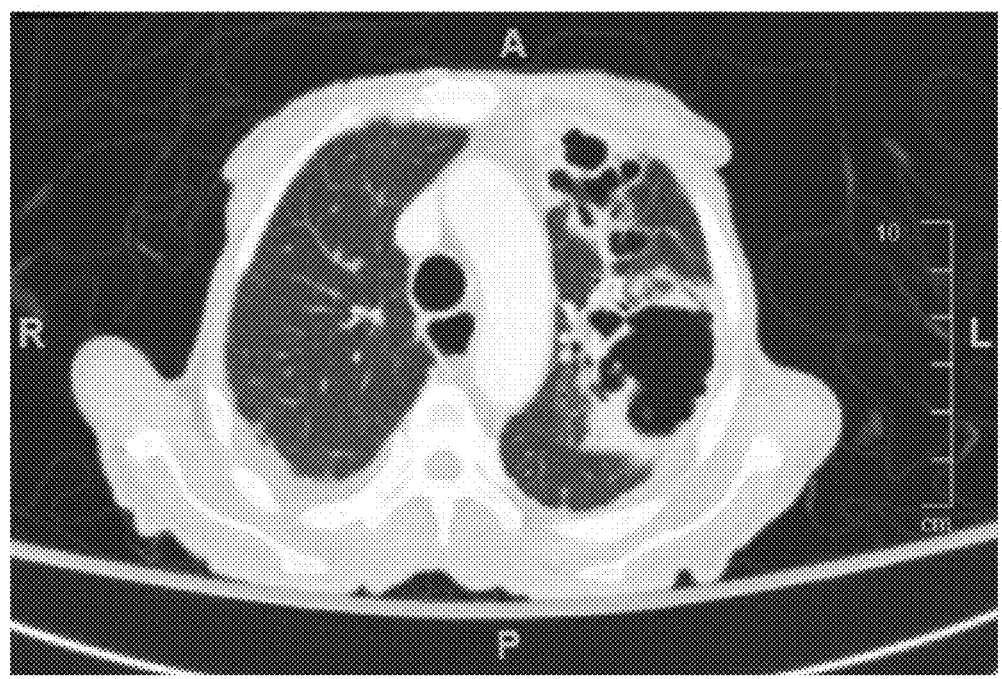

The oligonucleotides and method disclosed herein can be used to determine the presence of *M. riyadhense* in a biological or non-biological sample. The sample can be obtained from a subject such as a human subject.

19 Claims, 11 Drawing Sheets

Specification includes a Sequence Listing.

(56) References Cited

OTHER PUBLICATIONS

Crespi, et al., "Fasciation induction by the phytopathogen Rhodococcus fascians depends upon a linear plasmid encoding a cytokinin synthase gene", EMBO J., 11(3): 795-804 (1992).

Da Silva Rabello, et al., "First Description of Natural and Experimental Conjugation between Mycobacteria Mediated by a Linear Plasmid", PLoS One, 7(1):e29884, 8 pages (2012).

Delogu, et al., "Comparative Immune Response to PE and PE_PGRS Antigens of *Mycobacterium tuberculosis*", Infect. Immun., 69(9):5606-11 (2000).

Ding, et al., "Lymphadenitis caused by non_tuberculous mycobacteria in a university hospital in Taiwan: predominance of rapidly growing mycobacteria and high recurrence rate", J. Formos. Med. Assoc., 104(12): 897-904 (2005).

Edgar, "MUSCLE: a multiple sequence alignment method with reduced time and space complexity", BMC Bioinformatics, 5(113): 1-19 (2004).

Falkinham, Ecology of Nontuberculous Mycobacteria—Where Do Human Infections Come from?, Semin. Respir. Crit. Care Med., 34(1): 95-102 (2013).

Fedrizzi, et al., "Genomic characterization of Nontuberculous Mycobacteria", Sci. Rep. 2017; 7. DOI:10.1038/srep45258.

Garbati, "*Mycobacterium riyadhense* Lung Infection in a Patient with HIV/AIDS", Sub-Saharan African J. of Med., 1(1):56-58 (2014).

Godreuil, et al., "*Mycobacterium riyadhense* Pulmonary Infection, France and Bahrain", Emerg. Infect. Dis., 18( ):176-8 (2012).

Gutierrez, et al., "Ancient Origin and Gene Mosaicism of the Progenitor of *Mycobacterium tuberculosis*", PLoS Pathog., 1(1): 0055-0061 (2005).

Haubold, et al., "Genome comparison without alignment using shortest unique substrings", BMC Bioinformatics, 6(123): 1-11 (2005).

Houben, et al., "Takefive—Type VII secretion systems of Mycobacteria", Biochim. Biophys. Acta.—Mol. Cell Res., 1843: 1707-16 (2014).

Huerta-Cepas, et al., "eggNOG 4.5: a hierarchical orthology framework with improved functional annotations for eukaryotic, prokaryotic and viral sequences", Nucleic Acids Res, 44(D1):286-93 (2016).

Ihaka, et al., "R: A Language for Data Analysis and Graphics", J Comput Graph Stat., 5(3): 299-314 (1996).

Isom, et al., MCE domain proteins: conserved inner membrane lipid-binding proteins required for outer membrane homeostasis, Sci. Rep., 7(1):8608, 12 pages (2017).

Jang, et al., "Horizontally acquired genomic islands in the tubercle bacilli", Trends. Microbiol., 16(7): 303-8 (2008).

Jia, et al., "The Bioinformatics Analysis of Comparative Genomics of *Mycobacterium tuberculosis* Complex (MTBC) Provides Insight into Dissimilarities between Intraspecific Groups Differing in Host Association, Virulence, and Epitope Diversity", 7(88):1-14, Front Cell Infect. Microbiol., (2017).

Kim, et al., "Whole-Genome Sequence of a Novel Species, *Mycobacterium yongonense* DSM 45126",Genome Announc., 1(4): e604-13 (2013).

Kinashi, "Giant linear plasmids in Streptomyces: a treasure trove of antibiotic biosynthetic clusters", The J. of Antibiot., 64: 19-25 (2011).

King, et al., "Environmental reservoirs of pathogenic mycobacteria across the Ethiopian biogeographical landscape", PLoS One, 12:1-15 (2017).

Koren, et al., Canu: scalable and accurate long-read assembly via adaptive k-mer weighting and repeat separation, Genome Res., 27(5):722-36 (2017).

Kozak, et al., "Region of Difference 2 Contributes to Virulence of *Mycobacterium tuberculosis*", Infect. Immun., 79(1): 59-66 (2011).

Krumsiek, et al., "Gepard: a rapid and sensitive tool for creating dotplots on genome scale", Bioinformatics, 23(8): 1026-8 (2007).

Kumar, et al., Abstract 3706: Validation of human and mouse myeloid panels on the NanoString® nCounter® Platform. 2017: 3706-3706.

Leon, et al., "Molecular analysis of the linear 2.3 kb plasmid of maize mitochondria: apparent capture of tRNA genes", Nucleic Acids Res., 17(11): 4089-99 (1989).

Li, et al., "Fast and accurate short read alignment with Burrows-Wheeler transform", Bioinformatics, 25(14): 1754-60 (2009).

Li, et al., "OrthoMCL: Identification of Ortholog Groups for Eukaryotic Genomes", Genome Res., 13(9): 2178-89 (2003).

Morgado, et al., "Complete plasmid sequence carrying type IV-like and type VII secretion systems from an atypical mycobacteria strain", Mem. Inst. Oswaldo Cruz, 112(7):514-6 (2017).

Murty, et al., "A Brief review on Ecology and Evolution of Mycobacteria", Mycobact. Dis. 4(6): 1000172, 2 pages (2014).

Naeem, et al., "SVAMP: sequence variation analysis, maps and phylogeny", Bioinformatics, 30(15): 2227-9 (2014).

Narendrula-Kotha, et al., "Microbial Response to Soil Liming of Damaged Ecosystems Revealed by Pyrosequencing and Phospholipid Fatty Acid Analyses", PLoS One, 12(1):e0168497, 22 pages (2017).

Newton-Foot, et al., "The plasmid-mediated evolution of the mycobacterial ESX (Type VII) secretion systems", BMC Evol. Biol., 16(62):1-12 (2016).

Panwalker, et al., "Nosocomial *Mycobacterium gordonae* pseudoinfection from contaminated ice machines", Infect. Control., 7(2):67-70 (1986).

Park, et al., "Detection and Identification of Mycobacteria by Amplification of the Internal Transcribed Spacer Regions with Genus-and Species-Specific PCR Primers", J. Clin. Microbiol., 38(11): 4080-5 (2000).

Picardeau, et al., "Characterization of Large Linear Plasmids in Mycobacteria", J. Bacteriol., 179(8): 2753-6 (1997).

Ru, et al., "The Impact of Genome Region of Difference 4 (RD4) on Mycobacterial Virulence and BCG Efficacy", Front Cell Infect Microbiol., 7(239): 1-8(2017).

Saito, et al., *Mycobacterium shinjukuense* sp. nov., a slowly growing, non-chromogenic species isolated from human clinical specimens, Int. J. Syst. Evol. Microbiol., 61 (pt.8): 1927-32 (2011).

Seemann, "Prokka: rapid prokaryotic genome annotation", Bioinformatics, 30(14): 2068-9 (2014).

Singh, et al., "Missed Opportunities for HIV Testing of Patients Tested for Sexually Transmitted Infections at a Large Urban Health Care System From 2010 to 2015", Open Forum Infect. Dis., 5(7): S29-S29 (2018).

Slayden, et al., "Toxin-antitoxin systems and regulatory mechanisms in *Mycobacterium tuberculosis*", Pathog. Dis., 76(4):1-12 (2018).

Stamatakis, et al., RAxML-III: a fast program for maximum likelihood-based inference of large phylogenetic trees gram for maximum likelihood-based inference of large phylogenetic trees, Bioinformatics, 21(4): 456-63 (2005).

Stinear, et al., "Insights from the complete genome sequence of *Mycobacterium marinum* on the evolution of *Mycobacterium tuberculosis*", Genome Res., 18(5): 729-41 (2008).

Supply, et al., "Genome analysis of smooth tubercle bacilli provides insights into ancestry and pathoadaptation of the etiologic agent of tuberculosis", Nat. Genet., 45(2): 172-9 (2013).

Surtees, et al. " Plasmid and Chromosome Traffic Control: How ParA and ParB Drive Partition", Curr. Top Dev Biol., 56: 145-80 (2003).

Tortoli, et al., "Commercial DNA Probes for Mycobacteria Incorrectly Identify a No. of Less Frequently Encountered Species", J. Clin. Microbiol., 48(1): 307-10 (2010).

Tortoli, et al., "The new phylogeny of the genus *Mycobacterium*: The old and the news", Infect. Genet. Evol., 56: 19-25 (2017).

Uchiya, et al., "Characterization of a Novel Plasmid, pMAH135, from *Mycobacterium avium* Subsp. Hominissuis", PLoS One, 10(2): 1-18 (2015).

Ummels, et al., "Identification of a Novel Conjugative Plasmid in Mycobacteria That Requires Both Type IV and Type VII Secretion", MBio., 5(5):e01744-14, 8 pages (2014).

Van Der Werf, et al., "Inventory study of non-tuberculous mycobacteria in the European Union", BMC Infect. Dis., 14(62):1-9 (2014).

(56) References Cited

OTHER PUBLICATIONS

Van Der Woude, et al., "Unexpected Link between Lipooligosaccharide Biosynthesis and Surface Protein Release in *Mycobacterium marinum*", J. Biol. Chem., 287(24): 20417-29 (2012).

Van Ingen, et al., "Clinical relevance of non-tuberculous mycobacteria isolated in the Nijmegen-Arnhem region, The Netherlands", Thorax, 64(6): 502-6 (2009c).

Van Ingen, et al., "Global outbreak of severe *Mycobacterium chimaera* disease after cardiac surgery: a molecular epidemiological study", Lancet Infect Dis., 17(10): 1033-41 (2017).

Van Ingen, et al., "*Mycobacterium riyadhense* sp. nov., a non-tuberculous species identified as *Mycobacterium tuberculosis* complex by a commercial line-probe assay", Int. J. Syst. Evol. Microbiol., 59(Pt5): 1049-53 (2009b).

Van Ingen, et al., "Region of Difference 1 in Nontuberculous *Mycobacterium* Species Adds a Phylogenetic and Taxonomical Character", J. Bacteriol., 191(18): 5865-7 (2009a).

Van Soolingen, et al., "A novel pathogenic taxon of the *Mycobacterium tuberculosis* complex, Canetti: characterization of an exceptional isolate from Africa", Int. J. Syst. Bacteriol., 47(4): 1236-45 (1997).

Veyrier, et al., "Phylogenetic detection of horizontal gene transfer during the step-wise genesis of *Mycobacterium tuberculosis*", BMC Evol Biol., 9(196):1-14 (2009).

Wang, et al., "Insights on the Emergence of *Mycobacterium tuberculosis* from the Analysis of *Mycobacterium kansasii*", Genome Biol. Evol., 7(3): 856-70 (2015).

Weerdenburg, et al., "ESX-5-deficient *Mycobacterium marinum* is hypervirulent in adult zebrafish", Cell Microbiol., 14(5): 728-39 (2012).

Wu, et al., "Phylogenomic analysis of bacterial and archaeal sequences with AMPHORA2", Bioinformatics, 28(7): 1033-4 (2012).

Zrimec, et al., "DNA structure at the plasmid origin-of-transfer indicates its potential transfer range", Sci. Rep., 8(1):1820, 10 pages (2018).

* cited by examiner

COMPOSITIONS AND METHOD FOR DETECTING *MYCOBACTERIUM RIYADHENSE*

CROSS-REFERENCE TO RELATED APPLICATIONS

This application claims benefit of U.S. Provisional Application No. 62/884,203, filed on Aug. 8, 2019, which is hereby incorporated herein by reference in its entirety.

REFERENCE TO SEQUENCE LISTING

The Sequence Listing submitted Dec. 28, 2020, as a text file named "KAUST_2019-144-02_ST25" created on Dec. 28, 2020, and having a size of 6,972 bytes is hereby incorporated by reference pursuant to 37 C.F.R. § 1.52(e)(5).

FIELD OF THE INVENTION

The present disclosure relates to the field of *Mycobacterium* detection, more particularly, *Mycobacterium riyadhense*.

BACKGROUND OF THE INVENTION

Non-tuberculous mycobacteria (NTM), including *Mycobacterium riyadhense*, are ubiquitous, naturally occurring environmental bacteria, commonly found in water and soil (Falkinham, 2013) (J. Van Ingen et al., 2009). A wide range of animal and environmental sources (aquaria, swimming pools) act as reservoirs for NTM and several human disease outbreaks caused by exposure to environmental NTMs have been described (Ding et al., 2005) (Panwalker and Fuhse, 1986) (Carbonne et al., 2009) (Singh et al., 2018). With the ability to cause infections in both immunocompromised (Garbati and Hakawi, 2014) and immunocompetent (Choi et al., 2012) individuals, *M. riyadhense* has positioned itself as an important pathogen since its discovery in 2009 (van Ingen et al., 2009) as a cause of pulmonary infections. The clinical and radiologic characteristics of pulmonary infections caused by *M. riyadhense* are indistinguishable from those caused by *M. tuberculosis* (MTB) (Choi et al., 2012) (van Ingen et al., 2009).

Similar to *M. tuberculosis*, *M. riyadhense* grows at 37° C. and takes 2~3 weeks (van Ingen et al., 2009) to form visible colonies on laboratory media. However, unlike *M. tuberculosis*, which is a common world-wide pathogen transmitted directly from human to human with no known environmental reservoirs (King et al., 2017), *M. riyadhense* infections are rare and are transmitted to patients via contact with contaminated water (King et al., 2017) and soil (Narendrula-Kotha and Nkongolo, 2017), with no human to human transmission has been reported. Infections with *M. riyadhense* have been reported from Bahrain (Godreuil, et al., *Emerg. Infect. Dis.,* 18:176-8 (2012), France (Godreuil, et al., *Emerg. Infect. Dis.,* 18:176-8 (2012)), Italy (Van der Werf et al., 2014), Germany (Van deer Werf, et al., BMC *Infect. Dis.,* 1 14:62. doi: 10.1186/1471-2334-14-62 (2014)), and Korea (Choi, et al., *Ann Lab Med,* 32:298-303 (2012)) although most of the recent cases originate from Saudi Arabia (Althawadi, et al., *Emerg. Infect Dis.* 2017; 23: 2015-7). Indeed, the very first case of *M. riyadhense* infection was initially misdiagnosed as a case of *M. tuberculosis* infection in Saudi hospital using commercially available diagnostic tests (Tortoli, et al., *J. Clin. Microbiol.,* 48:307-10 (2010)).

Current literature indicates that *Mycobacterium canettii* is the most closely related obligate pathogenic species to the MTBC. Infections with *M. canettii* are extremely rare and found solely in people from the Horn of Africa, with no environmental reservoir yet described (Blouin et al., 2012). It is postulated that *M. tuberculosis* evolved from a free-living environmental ancestor into an obligate human pathogen. Previous phylogenetic studies have suggested that *Mycobacterium kansasii* or *Mycobacterium marinum, M. lacus, M. decipiens, M. shinjukuense, M. riyadhense* based on single marker gene (e.g. hsp65, 16s) are closely related to the free-living ancestor of the MTBC.

Due to the relatively recent emergence of *M. riyadhense* as an opportunistic human pathogen and its misdiagnosis by commercially available detection kits, an accurate set of diagnostic markers based on the genomic datasets generated in this study.

It is therefore an object of the present invention to provide compositions for detecting the presence of *M. riyadhense* in a sample.

It is also an object of the present invention to provide methods of detecting the presence of *M. riyadhense* in a sample.

SUMMARY OF THE INVENTION

Provided herein is at least one pair of oligonucleotides for use in amplifying at least one gene present in *M. riyadhense* comprising at least one forward primer and at least one reverse primer, wherein the forward primer comprises, consists essentially of or consists of SEQ ID NO:1, 3, 5, and 7 fragment(s), derivative(s), mutation(s), or complementary sequence(s) thereof and the reverse primer comprises, consists essentially of or consists of SEQ ID NO:2, 4, 6, and 8, fragment(s), derivative(s), mutation(s), or complementary sequence(s) thereof. Primer pairs provided herein include SEQ ID Nos:1 and 2; SEQ ID Nos:3 and 4; SEQ ID Nos:5 and 6; and SEQ ID Nos:7 and 8. The primers can be used to amplify at least one *M. riyadhense* gene selected from the group consisting of mr_00036, mr_00263, mr_00606, mr_01005 if present in a sample.

In one embodiment, amplification is carried out by PCR (polymerase chain reaction). In another embodiment, the amplification is isothermal amplification.

Also provided are methods for detecting the presence of *M. riyadhense* in a sample. The method includes contacting a biological sample with at least a pair of oligonucleotides described above, under conditions suitable for amplification of at least one gene product selected from of mr_00036, mr_00263, mr_00606, and mr_01005, if present, and detecting the presence of the amplification product. Preferred genes that can be amplified include SEQ ID Nos: 9, 10, 13 and 14. In a preferred embodiment, the method of amplification comprises carrying out a polymerase chain reaction (PCR).

The oligonucleotides and method disclosed herein can be used to determine the presence of *M. riyadhense* in a biological or non-biological sample. In a preferred embodiment, the sample is obtained from a human subject.

In a further embodiment, a kit for detecting one or more nucleic acids of *M. riyadhense* is provided. The kit can include one or more sets of primers specific for amplification of *M. riyadhense* gene target; and one or more detectable probes specific for detection of the amplification products.

In one aspect, the kit can include probes already labeled with donor and corresponding acceptor moiety, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of *M. riyadhense* in a sample.

BRIEF DESCRIPTION OF THE DRAWINGS

FIG. 1 is an axial enhanced CT scan of the chest from host of MR193. Multifocol cavitating consolidation in both lungs predominantly involving the left upper lobe associated with ill-defined ground-glass centritobulor nodules and tree-in-bud appearance on both lungs. The findings suggestive of tuberculosis.

FIGS. 2A and 2B show Genome content comparison. Venn diagrams represents the overlap of gene orthologs between the (A) *M. riyadhense, M. tuberculosis*, H37Rv, *M. marinum* M, *M. kansasii* 12478 and *M. szulgai* and (B) *M. riyadhense* and five species within MTBC.

FIGS. 3A-I show LOS systems in *M. riyadhense* and other related mycobacteria and 2D-TLC analysis of polar lipids extracted from selected *M. riyadhense* strains. (FIG. 3A) Genetic locus map of the LOS biosynthesis gene cluster from *M. riyadhense, M. canettii* A and *M. tuberculosis* H37Rv (drawn to scale). The arrows showing the direction of transcription and the genes are colored according to the orthologous relationships. The Genetic locus map is split at FadD24. The complete map has the right pointing arrow for FadD24, next to the left pointing arrow for mmpL12 (FIG. 3B) Rough-dry colony morphology (MR193) and (FIG. 3C) smooth morphology (MR226) of *M. riyadhense*. Polar lipids from two known LOS producers, *M. marinum* (FIG. 3D) and *M. kansasii* (FIG. 3E) are included to show the migration pattern of LOS species in System E. (FIG. 3F) 2D-TLC analysis of polar lipids extracted from select *M. riyadhense* rough strain or smooth (FIG. 3G) strain. A separate staining with alpha-naphthol also confirmed that this was a glycolipid species from the same (FIG. 3H) rough and (FIG. 3I) smooth strain. (FIG. 3D), (FIG. 3E), (FIG. 3F) and (FIG. 3G) were charred after staining with MPA, while (FIG. 3H) and (FIG. 3I) were charred after staining with alpha naphthol. LOS III from *M. riyadhense* is indicated by a solid arrow.

FIG. 4 shows the genetic locus map of the pe-pgrs33 gene cluster from *M. marinum, M. kansasii, M. riyadhense, M. canettii* and *M. tuberculosis* (drawn to scale). The arrows showing genes are colored according to the orthologs. The deletion event was highlighted in red while the insertion event in green.

FIG. 5 is a comparison of different gene clusters that encode type VII secretion systems in MR226 strain. The color coding for the figure is presented in the key. The black arrows indicate region-specific genes.

FIG. 6 shows an agarose gel (2%) electrophoresis analysis of a PCR diagnostic test for *M. riyadhense*. Lane M: DNA Marker, Lane 1-8: Varies *M. riyadhense* strains (From left to right: MR193, MR206, MR210, MR222, MR226, MR244, MR246, MR1023), Lane 9-16: Varies *Mycobacterium* species (From left to right: *M. tuberculosis, M. bovis, M. africanum, M. microti, M. oryis, M. kansasii, M. szulgai* and *M. angelicum*) template, Template cocktail, *Mycobacterium* species (*M. tuberculosis, M. bovis, M. kansasii, M. marinum, M. szulgai, M. avium* and *M. angelicum*) with (Lane 17, +) and without (Lane 18, −) *M. riyadhense* MR226 gDNA template. Lane 19: Non-template control (NTC). Upper Panel: MRDP (*M. riyadhense* diagnostic marker) set. Lower Panel B: *Mycobacterium* genus specific primer ITS-T and mycom-R amplified with mycobacterial gDNA.

DETAILED DESCRIPTION OF THE INVENTION

I. Definitions

As used herein, the term "amplifying" refers to the process of synthesizing nucleic acid molecules that are complementary to one or both strands of a template nucleic acid molecule.

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released.

The term "5' to 3' nuclease activity" refers to an activity of a nucleic acid polymerase, typically associated with the nucleic acid strand synthesis, whereby nucleotides are removed from the 5' end of nucleic acid strand.

II. Compositions

Compositions and kits useful for detecting the presence of *M. riyadhense* in a sample are provided. The compositions include the oligonucleotide primers that can be used to at least one *M. riyadhense* gene selected from the group consisting of mr_00036, mr_00263, mr_00606, mr_01005 if present in a sample. A gene sequence encoding MR_00036 hypothetical protein is provided below.

(SEQ ID NO: 9)

```
GTGCGCCCGGCGCCGATCCGGGTGCTTCGTTGTCGGTTTCGTCGCGATAA
CGATGACGGCGTGGGCGCCGGTGTTCTTGCGGAGGCTCGGACGCCGGTTC
AGGTGGGGGCGCGGCGGGTTGCGCGGGCCCGCCGATCCGGACGCGGCGCG
GTAACGGCCCCGGCGGCGCCGGCGGCGCCGGCGGCGCTTGCGGCGGTCCG
TTCGATGGCGGCGGCGGTGGCTTGGGCGGTGCTGGCGGGGAGCTGGCCTT
CGGCGCATGAGCCGACGGTCGTTGCGGCGCTGCCACCGCGGCGCGCACCG
GCCCGTTGGATGTTGGCGGTGGCGGTGGTTGGGGAGGGGCCTGGGGGGGT
CCGCCGATTGGCATCCTCGGAGTACCGGTTTTCGGTGGAGCTGACGCTCG
TGGGGACGGGGGTGGCGGCGTGGGGGGTTGGGGAGGGGCCTGCGGCCGTC
CGCCGATGGGCATGGGGGGTGCCGGTGGTTTGGGCGGAGCACCCGTTGGT
TCGGCCGAAGCCAGTGGCGGTTCGGGTGGCGCGGGTGGCGGTTCGGCCGA
AGCCAGTGGCGGTTCGGGTGGCGCGGGTGGCGGTTCGGGTGGCGCGGGTG
GCGGTTCGGGTGGCGCGGGTGGAGTTGGCGGCGGTCCGCCGATGGGCATG
GGGGGCGCCGGTGGTTTGGGCCCAGCTGCGGCGGGCCCGGCAGTTGCGGT
TGCGGCGGACGGCCATTCGGGTGGCGCCGGCGGTTCGGGCAGCGGCGGCG
GCGGTTCGGGTGTGGGCGGCGGCGGTGCGGGTGTGGGCGGCGGCGGTGCG
GGTGTGGGCGGCGGCGGTGCGGGTGTGGGCGATTGCGCCCCGCCGCCGAT
```

TGGCATTGGAGCCGGCGGCGGTTCGGGTGGCGCCGGCGGAGGCTCTACCG

GGGACGTAG.

A sequence encoding MR_00263 hypothetical protein is shown below.

(SEQ ID NO: 10)
TTGATCGGCAACGGCGGCGCCGGCGGGTCCGGTGCCACCGCTGTTGGCGA

CGGTAAGGCCGGCGGTAACGGCGGGCCCGCCGGGCTGTTCGGCAACGGCG

GGGCAGGCGGGGCCGGCGGGAACTCACTGAGCGGCACCGGCGGGGCCGGC

GGCCGTGGCGGCGACGCCATGCTGTTCGGCAACGGCGGCCCCGGCGGGGC

CGGCGGGTGGGCAGGGGGCACTGCCCAAGTCGCCGGGGCCGGCGGGGCCG

GCGGCAACGCCGGTTCGCTCTTCGGCGCCGCCGGGACCGGCGGCGTCGGA

GGGTCCGCCACAGACACCGGCGGTGACGGCGGGCCCGGCGGGGCCGGCGG

GGCCGGCGGGATGTTCGCCAGCGGCGGGGCCGGCGGGGCCGGCGGGTCTG

GCGGCAACACCGACGGTGACGCGGGGCCGGCGGGGCCGGCGGGGCCGGC

GGGCTGTTCGGCGCCGGCGGTGACGGCGGGGCCGGCGGGGCTGGCGGGAC

CACCGCCACCGGCGGGGCCGGCGGGGCCGGGGCAACGCCGGCATGCTCT

CGGTCGGTGCCGCCGGCGGCGCCGGCGGCAGCGGCGGGTCCGGGGACGGT

ATCGGCGGTGACGGCGGGGCCGGTGGGACCGGCAGCTTAATCTTGGGCGC

CGGCGGCGCCGGCGGCGCCGGCGGCAGCGGCGGGACCACGGTTAGCCCCG

GCATCGGCGGGGCCGGCGGGGTAGGTGGGGCCGGCGGCTTAGTCATAGGC

TCTGGCGGCAGCGGCGGCGCCGGCGGGTTCGGCACCATCACCGGCGGGGC

CGGCGGGGCCGGCGGCAAGCCCGGACTGATTGGCAATGGCGGTGACGGGG

GTACCGGAGGCGACGGCGGCATCGGCGGCGGCGCCGGTGGGGCCGGCGGC

AACGCCGTGCTGATCGGCAACGGCGGCAACGCGGCAACGGCGGTGGCTT

CGGGCCCGTCAAGGGCAACGGCGGCACCGGCGGCACGGGCGGGCTGCTGC

TCGGCCTGAACGGGATCAACGGGACGAAGGGCGTATAG.

A sequence encoding MR_00606 hypothetical protein is shown below (SEQ ID NO: 13)
ATGATTGATTCGATGTCGGCGGCGCTGACCGCCGTCACCCTGATCGAGAC

CGCCGTCGGTGCGGACGACCGTCTACAGATCGCGGCCGCCCTCCTGCCCG

ACAACCTGCCCGATACGCACTTGGTGCTCTCAAGCGCGGTGTGGTGCGCG

CACCACTTGGCCGAGTCGTTGGCCGAGGAGCTTGGCGTCGACATCGCAAC

CGTCAAGGCGGCGCTGCGCGACGAGGTGGCCGAACGATTCCAGAACTACA

ACCCCACGGAGGAACAGTGA.

A sequence encoding MR_01005 hypothetical protein is shown below.

(SEQ ID NO: 14)
GTGGACCGACGCAGCAAAGCAGCCTGCGGGTCGGCCGGACTGTGGGGTAA

CGGTGGAGCAGGCGGCGCCGGCGGAACGGGCACGGCCGGGATCAATGGCG

GGGCCGGCGGCGCCGGCGGCAACGGCGGACTGCTCTCCGGCGCCGGCGGG

GCCGGCGCCCACGGCGGTGCTGGAATTGCCGGCGGGCCGGGCCTGGCCGG

AGGTGCCGGCGGTGACGGCGGAGCCGGCGGCAAGGGCGGCCTGTGGATGG

GCCAGGGCGGCGCGGGCGGGCAAGGAGGTGACGGCGGCGCTGGCGGCGTC

GGCACTACCGGTCTGACGGGCAGCATCGGCGGCCAAGGCAGTACCGGCGG

CAACGGCGGCGCCCGCGGCGATAGCGGTGTCGGCGGCACTAACGGCAGCG

GCGGCCGTGGCGGCGACGGTGGCATCGGCGGCACCGGCGGCACCGGCGGC

ACCGGCGGCGCCGGCACCACAACTATGGCCGGGGGGACCGGCGGCAACGG

CGGCGACGGCGGCAACGGTGGTGCAAACGGAGTAGGCGACATCACCGGCA

TCCCTGTCGCTGGCTCCGACGGTGTCGGCGGCGACGGCGGCTTCGGCGGC

GACGGCGGCGACGGCGGCACTACAGGCGGCGTCGGCGCGAGCGGTGGCGC

GGGCGGCAACGGCGGTGCCGGCGACGGAGGAGCGGCTGGCACCGGCTCAC

CCGGCACCCCCGGCACGCCGAACGCGGGTACCTCGGGCGGCGACGGCGGG

ACCGGAGGGGCGGGTGGCTCTGGTGGGGGGCCCACATAG.

Preferred primers comprises, consists essentially of or consists of:

(SEQ ID NO: 1)
MRDP-MR_00036-F (5'-TTCGTTGTCGGTTTCGTCGC-3');

(SEQ ID NO: 2)
MRDP-MR_00036-R (5'-GCGTCAGCTCCACCGAAAAC-3');

(SEQ ID NO: 3)
MRDP-MR_00263-17 (5'-CCACCGCTGTTGGCGA-3');

(SEQ ID NO: 4)
MRDP-MR_00263-R (5'- TTCGTCCCGTTGATCCCGTT -3');

(SEQ ID NO: 5)
MRDP-MR_00606-F (5'- AACCTGCCCGATACGCACTT -3');

(SEQ ID NO: 6)
MRDP-MR_00606-R (5'- ACTGTTCCTCCGTGGGGTTG -3');

(SEQ ID NO: 7)
MRDP-MR_01005-F (5'- GACTGTGGGGTAACGGTGGA -3');

(SEQ ID NO: 8)
MRDP-MR_01005-R (5'- CCGGTGATGTCGCCTACTCC -3').

The disclosed primers specifically anneal to nucleic acid sequence encoding MR-0036, 00263, 00606 and 01005, and initiate DNA synthesis therefrom under appropriate conditions producing the respective amplification products.

The oligonucleotide primer sequence may be between 13 and 35 linked nucleotides in length and may comprise at least 70% sequence identity to SEQ ID NOs:1-8. A skilled person will appreciate that a given primer need not hybridize with 100% complementarity in order to effectively prime the synthesis of a complementary nucleic acid strand in an amplification reaction.

Accordingly, the primers van be variants of SEQ ID NOs:1-8. A primer may hybridize over one or more segments such that intervening or adjacent segments are not involved in the hybridization event, (e.g., for example, a loop structure or a hairpin structure). In particular, the sequence of the oligonucleotide may have 80%, 85%, 90%, 95% or 98% sequence identity to SEQ ID NOs:1-8. An extent of variation of 70% to 100%, or any range therewithin, of the sequence identity is possible relative to the specific primer sequences disclosed. Determination of sequence identity is described in the following example: a primer 20 nucleotides in length which is identical to another 20 nucleotides in length primer having two non-identical residues has 18 of 20 identical residues (18/20=0.9 or 90% sequence identity). In another example, a primer 15 nucleotides in length having all residues identical to a 15 nucleotides segment of primer 20 nucleobases in length would have 15/20=0.75 or 75% sequence identity with the 20 nucleotides primer.

Those of skill in the art readily understand how to determine the homology of two proteins or nucleic acids, such as genes. For example, the homology can be calculated after aligning the two sequences so that the homology is at its highest level. Another way of calculating homology can be performed by published algorithms. Optimal alignment of sequences for comparison can be conducted by the local homology algorithm of Smith and Waterman, *Adv. Appl. Math.* 2: 482 (1981), by the homology alignment algorithm of Needleman and Wunsch, *J. Mol Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. The same types of homology can be obtained for nucleic acids by for example the algorithms disclosed in Zuker, *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein. For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

III. Methods for Detection and Treatment

Methods for the rapid detection of the presence or absence of *M. riyadhense* in a biological or non-biological sample are provided. The disclosed primers can be employed in a nucleic acid test to detect the presence of *M. riyadhense* in a sample. "A nucleic acid test (NAT) or nucleic acid amplification test (NAAT) is a technique utilized to detect a particular nucleic acid, virus, or bacteria which acts as a pathogen in blood, tissue, urine, etc. The NAT system differs from other tests in that it detects genetic materials rather than antigens or antibodies. Since the amount of a certain genetic material is usually very small, NAT includes an amplification step of the genetic material.

The presence of *M. riyadhense* can be determined using Polymerase Chain Reaction (PCR), or isothemal amplification to amplify genes from *M. riyadhense* present in the sample. In some optional embodiments, DNA is extracted from the sample to be assayed using known method for extracting DNA from a sample.

In one embodiment, a method for detecting *M. riyadhense* in a sample is provided, includes performing an amplifying step including contacting the sample with a set of primers to produce an amplification product (amplicon) if riyadhense is present in the sample and detecting the presence or absence of the amplified product, wherein the presence of the amplified product is indicative of the presence of *M. riyadhense* in the sample and wherein the absence of the amplified product is indicative of the absence of *M. riyadhense* in the sample. The primers are designed to amplify one or more genes selected from the group consisting of mr_00036, mr_00263, mr_00606, and mr_1005 genes. The sets of primers are preferably selected from the group consisting of SEQ ID Nos:1 and 2; SEQ ID Nos:3 and 4; SEQ ID Nos:5 and 6; SEQ ID Nos:7 and 8. Embodiments include methods of detection of *M. riyadhense* comprising performing at least one cycling step, which may include an amplifying step.

Preferred amplification products is an amplification product of SEQ ID NO. 9, 10, 13 or 14. The amplification products have sizes of about 994 bp base pairs), 511 bp, 372 bp or 166 bp in size. The method can includes amplifying SEQ ID NO:9, if present in the sample. The method can includes amplifying SEQ ID NO:10, if present in the sample. The method can includes amplifying SEQ ID NO:13, if present in the sample. The method can includes amplifying SEQ ID NO:14, if present in the sample. The method can include amplifying any combination of SEQ ID Nos:9, 10, 13 and 14. The amplification product can have a size of about 372 bp. The amplification product amplification can have a size of about 994 bp. The amplification product can have a size of about 166 bp. The amplification product can a size of about 511 bp. Detection of the any amplification products of SEQ ID Nos: 9, 10, 13 or 14 as disclosed herein, indicates the presence of *M. riyadhense* in the sample.

The method in some embodiments includes an internal control molecules and one or more detectable probes. The term "internal control (IC) molecule" is herein defined as the in vitro transcribed oligonucleotide molecule which is co-amplified by the same primer set for *M. tuberculosis* used in the method of the present invention. In particular, the IC may be mixed in the reaction mixture to monitor the performance of PCR to avoid false negative results. The probe to detect this IC molecule may be specific to the interior part of this molecule. This interior part may be artificially designed and may not occur in nature. In some embodiments, the ITS-F/mycom-2 primer set (5'-TGGATCCGACGAAGTCGTAACAAGG-3' (SEQ ID NO:11)/ 5'-TGGATAGTGGTTGCGAGCAT-3' (SEQ ID NO:12)

(Park, et al., *J. Clinical. Microbiol.*, 38:4080-5 (2000)) which is a *Mycobacterium* genus-specific primer set can be used as a control.

(A) Polymerase Chain Reaction (PCR)

Conventional PCR techniques are known in the art. PCR typically employs two oligonucleotide primers that bind to a selected nucleic acid template (e.g., DNA or RNA). Each PCR assay requires the presence of template DNA, primers, nucleotides, and DNA polymerase. The DNA polymerase is the key enzyme that links individual nucleotides together to form the PCR product. The nucleotides include the four bases adenine, thymine, cytosine, and guanine (A, T, C, G)—that are found in DNA. These act as the building blocks that are used by the DNA polymerase to create the resultant PCR product. The primers in the reaction specify the exact DNA product to be amplified. The primers are short DNA fragments with a defined sequence complementary to the target DNA that is to be detected and amplified. These serve as an extension point for the DNA polymerase to build on. The above mentioned components are mixed in a test tube or 96-well plate and then placed in a machine that allows repeated cycles of DNA amplification to occur in three basic steps. The machine is essentially a thermal cycler. It has a thermal block with holes, into which the test tubes or plates holding the PCR reaction mixture are inserted. The reaction solution is first heated above the melting point of the two complementary DNA strands of the target DNA, which allows the strands to separate, a process called denaturation. The temperature is then lowered to allow the specific primers to bind to the target DNA segments, a process known as hybridization or annealing. Annealing between primers and the target DNA occurs only if they are complementary in sequence (e.g. A binding to G). The temperature is raised again, at which time the DNA polymerase is able to extend the primers by adding nucleotides to the developing DNA strand.

Primers useful in some embodiments include oligonucleotides capable of acting as points of initiation of nucleic acid synthesis of mr_00036, mr_00263, mr_00606, and mr_01005 genes (e.g., SEQ ID NOs: 1-8). A primer can be purified from a restriction digest by conventional methods, or it can be produced synthetically. The primer is preferably single-stranded for maximum efficiency in amplification, but the primer can be double stranded. Double stranded primers are first denatured, i.e., treated to separate the strands. One method of denaturing double stranded nucleic acids is by heating.

The template nucleic acid need not be purified; it may be a minor fraction of a complex mixture, such as nucleic acid contained in human cells present in a biological sample. Biological samples can be processed (e.g., by nucleic acid extraction methods and/or kits known in the art) to release nucleic acids or in some cases, the biological sample can be contacted directly with the PCR reaction components and the appropriate oligonucleotides. Nucleic acid molecules may be extracted from a biological sample by routine techniques such as those described in Diagnostic Molecular Microbiology: Principles and Applications (Persing et al. (eds), 1993, American Society for Microbiology, Washington D.C.).

Where the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min). In a particularly preferred method, denaturation is performed at about 94° C. for about 30 mins. The denaturation step is followed by primer annealing and extension.

The oligonucleotide primers pairs (e.g., SEQ ID NOs: 1-10) are combined with PCR reagents under reaction conditions that induce primer extension. For example, chain extension reactions generally include 50 mM KCl, 10 Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules being amplified. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, hut may be repeated as many as 40, 60, or even 100 times.

Suitable thermostable polymerases that can be used in a PCR reaction are known in the art. The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacreus, T. rubens, Bacillus stearothermophilus*, and *Methanothermus fervidus*. Nonetheless, polymerases that are not thermostable also can be employed in PCR assays provided the enzyme is replenished.

The method may be used for determining the identity and quantity of *M. riyadhense* in a sample comprising contacting the sample with a pair of primers according to any aspect of the present invention and a known quantity of a calibration polynucleotide comprising a calibration sequence, concurrently amplifying nucleic acid from the *M. riyadhense* in the sample with the pair of primers and amplifying nucleic acid from the calibration polynucleotide in the sample with the pair of primers to obtain a first amplification product comprising a *M. riyadhense* s identifying amplicon and a second amplification product comprising a calibration amplicon, obtaining molecular mass and abundance data for the *M.*

*riyadhense* identifying amplicon and for the calibration amplicon wherein the 5$^1$ and 3' ends of the *M. riyadhense* identifying amplicon and the calibration amplicon are the sequences of the pair of primers or complements thereof, and distinguishing the *M. riyadhense* identifying amplicon from the calibration amplicon based on their respective molecular masses, wherein the molecular mass of the *M. riyadhense* identifying amplicon indicates the identity of the *M. riyadhense*, and comparison of *M. riyadhense* identifying amplicon abundance data and calibration amplicon abundance data indicates the quantity of *M. riyadhense* in the sample.

The method according to any aspect of the present invention may further comprise a step of mixing an internal molecule (IC) and a probe specific to the IC with the biological sample. The use of the IC may improve the efficiency of the TB diagnosis increasing the accuracy of results.

The resultant PCR products (amplicons) can be visualized using any method known in the art. There are two main methods of visualizing the PCR products: (1) staining of the amplified DNA product with a chemical dye such as ethidium bromide or SyberSafe™, which intercalates between the two strands of the duplex or (2) labeling the PCR primers or nucleotides with fluorescent dyes (fluorophores) prior to PCR amplification and subsequent detection using UV light source and imaging system. The latter method allows the labels to be directly incorporated in the PCR product. The most widely used method for analyzing the PCIS product is the use of agarose gel electrophoresis, which separates DNA products on the basis of size and charge. Agarose gel electrophoresis is the easiest method of visualizing and analyzing the PCR product. It allows for the determination of the presence and the size of the PCR product. A predetermined set of DNA products with known sizes are run simultaneously on the gel as standardized molecular markers to help determine the size of the product.

Quantitative real-time or qRT-PCR provides information beyond mere detection of DNA. It indicates how much of a specific DNA or gene is present in the sample. qRT-PCR allows for both detection and quantification of the PCR product in real-time, while it is being synthesized. The two common methods used to detect and quantify the product include (1) fluorescent dyes that non-specifically intercalate with double-stranded DNA and (2) sequence-specific DNA probes consisting of fluorescently labeled reports. These permit detection only after hybridization of the probe with its complementary DNA target. Real-time PCR can be combined with reverse transcription, which allows messenger RNA to be converted into cDNA (i.e., reverse transcription), after which quantification of the cDNA is performed with qPCR. (reviewed in Garibaya, et al., *J. Invest Dermatol.,* 133 (3):e6 (2013)

Real-time PCR employs fluorescent dyes or probes that interact with the PCR products. The two primary types of fluorescent detection are DNA binding dyes, such as SYBR™ Green (cyanine dye), or fluorescently tagged sequence-specific probes, such as TaqMan™ or Molecular Beacon probes. When the DNA binding dyes attach to any double-stranded DNA segment, they emit a fluorescent signal. When in the presence of single-stranded nucleic acids, these dyes do not attach to the NA and emit only low levels of fluorescence. Although SYBR™ Green is commonly used, several other DNA binding dyes are also utilized. These include SYTO 9, SYTO-13, SYTO-82, (Thermofisher Scientific), (cell-permeant cyanine nucleic acid stains) and EvaGreen® (green fluorescent nucleic acid dye) (GOLGBIO). Since detection of a fluorescent signal from these dyes is not sequence-specific, melting temperature analysis must be performed to ensure the production of a single PCR product.

Nuclease dependent probes: Sequence-specific fluorescently labeled probes are the second main type of detection chemistry utilized in Real-time PCR. These probe systems can be nuclease dependent or simply hybridization probes. The nuclease cleaved probes include TaqMan, HybProbe (two oligonucleotides), minor groove binding (MGB), and locked nucleic acid (LNA) probes. These probes are complementary to a target nucleic acid sequence within the PCR amplicon, and they have both a reporter and a quencher fluorophore covalently attached to opposing ends. These systems utilize Florescent Resonance Energy Transfer (FRET) technology. When the dyes remain near one another, the fluorescent signal of the reporter dye is quenched, preventing any detectable signal. When the dyes are separated, the reporter dye's fluorescence is unquenched and thus detectable. A probe anneals to a sequence internal to the PCR primers' binding sites, and as the Taq DNA Polymerase enzyme extends the primers to produce the PCR product, its 5' exonuclease activity cleaves the end of the probe. The cleavage removes the quencher dye and allows excitation of the reporter dye, resulting in a fluorescent signal. Cycling probe technology (CPT) probes differ from the TaqMan type probes in that they include an RNA nucleotide. These probes form an RNA-DNA duplex upon hybridization to the target sequence. Then RNase H enzyme is used to cleave the quencher dye from the probe.

Hybridization probes: Although hybridization probes are also sequence-specific, they do not require the exonuclease cleavage of a dye from the probe. These include Molecular Beacons, which have a loop region between two inverted repeats, creating a hairpin structure. When the probe is denatured and anneals to a target sequence, the hairpin is released, and the fluorophores are separated from one another enough that the reporter dye generates increased fluorescence. Other detection probe technologies include the Scorpion (probe and one PCR primer are combined in one molecule), and LUX (Light Upon eXtension) assays. The Lux primer probe has a dye near its 3' end that is quenched by the hairpin structure of the primer. Once it binds to a target sequence and DNA polymerase extends the sequence, the dye's signal increases (reviewed in Walker-Daniels, MATER METHODS 2012, 2:119).

B. Isothermal Amplification

In contrast to PCR, isothermal amplification enables rapid and specific amplification of DNA at constant temperature (60-65° C.) avoiding the requirement of thermal cycling, which is applied in regular PCR. Four examples of sequence-specific isothermal DNA amplification technologies include:

(i) Loop-mediated isothermal amplification (LAMP): uses 4-6 primers recognizing 6-8 distinct regions of target DNA. A strand-displacing DNA polymerase initiates synthesis and 2 of the primers form loop structures to facilitate subsequent rounds of amplification. LAMP is rapid, sensitive, and amplification is so extensive that the magnesium pyrophosphate produced during the reaction can be seen by eye, making LAMP well-suited for field diagnostics. In LAMP, the target sequence is amplified at a constant temperature of 60-65° C. using either two or three sets of primers and a polymerase with high strand displacement activity in addition to a replication activity.

Typically, 4 different primers are used to identify 6 distinct regions on the target gene, which adds highly to the specificity. An additional pair of "loop primers" can further accelerate the reaction. Thus primers targeting regions in *M. riyadhense* genes mr_00036, mr_00263, mr_00606, mr_01005 can be designed for LAMP. Detection of amplification product can be determined via photometry for turbidity caused by an increasing quantity of magnesium pyrophosphate precipitate in solution as a byproduct of amplification.

The reaction can be followed in real-time either by measuring the turbidity or by fluorescence using intercalating dyes such as SYTO 9. Dyes such as SYBR green, can be used to create a visible color change that can be seen with the naked eye without the need for expensive equipment, or a response that can more accurately be measured by instrumentation, Dye molecules intercalate or directly label the DNA, and in turn can be correlated to the number of copies initially present. Hence, LAMP can also be quantitative. In-tube detection of DNA amplification is possible using manganese loaded calcein which starts fluorescing upon complexation of manganese by pyrophosphate during in vitro DNA synthesis. Moreover, visual detection of the LAMP amplicons by the unaided eye is based on their ability to hybridize with the complementary gold-bound ss-DNA. and thus prevent the normal red to purple-blue color change that would otherwise occur by salt-induced aggregation of the gold particles (ii) Strand displacement amplification (SDA) relies on a strand-displacing DNA polymerase, typically Bst DNA Polymerase, Large Fragment or Klenow Fragment (3'-5' exo-), to initiate at nicks created by a strand-limited restriction endonuclease or nicking enzyme at a site contained in a primer. The nicking site is regenerated with each polymerase displacement step, resulting in exponential amplification. SDA is typically used in clinical diagnostics;

(iii) Helicase-dependent amplification (HDA): employs the double-stranded DNA unwinding activity of a helicase to separate strands, enabling primer annealing and extension by a strand-displacing DNA polymerase. Like PCR, this system requires only two primers. HDA has been employed in several diagnostic devices and FDA-approved tests; and (iv) Nicking enzyme amplification reaction (NEAR): employs a strand-displacing DNA polymerase initiating at a nick created by a nicking enzyme, rapidly producing many short nucleic acids from the target sequence. This process is extremely rapid and sensitive, enabling detection of small target amounts in minutes. NEAR is commonly used for pathogen detection in clinical and biosafety applications.

Any isothermal amplification method known in the art can be used with the disclosed primers. Liu et al., Scientific Reports, 5 (12723) (2015), incorporated herein by reference, discloses an isothermal nucleic acid amplification method only requires one pair of primers and one enzyme, termed Polymerase Spiral Reaction (PSR) with high specificity, efficiency, and rapidity under isothermal condition.

C. Sample Types

Samples that are useful in the methods disclosed herein include any sample that contains nucleic acids (RNA or DNA). The disclosed oligonucleotides may be used in a method for the detection of *M. riyadhense* from either a clinical or a culture sample. Exemplary clinical samples include sputum, breast milk, semen, bronchoalveolar lavage fluid, pleural fluid, urine, bronchial aspirate, pleural fluid, ascetic/peritoneal fluid, cerebrospinal fluid (CSF), pus, stool, amniotic fluid, menstrual blood, peripheral blood or other body fluids, lymph node, pus or other aspirate and tissue biopsies.

In a preferred embodiment, the sample is obtained from a human subject.

Detection of the presence of *M. riyadhense* in a sample from a subject can be followed by an appropriate treatment regimen, preferably, and antibiotic regimen. Suitable antibiotic treatments include but are not to rifampin, ethambutol, clarithromycin, rifabutin, linezolid, amikacin, moxifloxacin (MOXI), ciproflaxacan, and trimethoprim-sulfamethoxazole (TMP-SMX).

The disclosed methods will be further understood by the following non-limiting examples.

EXAMPLES

Methods and Materials

Case Definition and Bacterial Strains

Eight *M. riyadhense* strains were collected in Riyadh, Saudi Arabia, between June 2011 and March 2016 (see in Table 1) from patients with a positive culture for *M. riyadhense* isolated from the microbiology laboratory at the King Fahad Medical City (KFMC) hospital in Riyadh, Saudi Arabia.

TABLE 1

| Clinical Characteristics of the Studied Population |
|---|
| All male<br>* Auramine-rhodamine stain, 4+; remaining strains N/A.<br># Rough<br>xx Smooth |

The sites of infection were as follows: MR193, MR206, MR210, and MR1023—Pulmonary; MR222—Pulmonary, LM, Abdominal; MR226—Pulmonary, LA; MR 244—Pulmonary, LN, Abdominal, Peritoneal; MR246—Pulmonary, Mediastinal LN.

TABLE 1

Clinical characteristics of the studied population

| | | | | | Therapy | | Ratiographic | Baseline | |
|---|---|---|---|---|---|---|---|---|---|
| | Age (Years) | HIV status | Other co-morbid conditions | Ziehl-Neelsen stain | Initial medication/ duraton | Continuous medication/ duration | Location of Lesion (Chest CT) | CD4 count ($\times10^9$/L) | Viral load (Copies/ mL) |
| NR193*# | 82 | Unknown | Smoking; DM; HTN; heart disease | 2+ | NA | NA | Left upper lobe consolidation | NA | N/A |

TABLE 1-continued

Clinical characteristics of the studied population

| | Age (Years) | HIV status | Other co-morbid conditions | Ziehl-Neelsen stain | Therapy | | Ratiographic | Baseline | |
| | | | | | Initial medication/ duraton | Continuous medication/ duration | Location of Lesion (Chest CT) | CD4 count (×10⁹/L) | Viral load (Copies/ mL) |
|---|---|---|---|---|---|---|---|---|---|
| MR206# | 32 | Negative | Eisenmenger's syndrome; pulmonary HTN | 1+ | IMP/2M CLR/2M EMB/2M INH/1M PYZ/1M RIF/1M | CLR/4M EMB/4M | Bilateral air spice consolidation and modular opacity | NA | N/A |
| MR210✕✕ | 66 | Positive | PCP co-infection | Negtive | EMB/18M CLR/18M | NA | Bilateral ground glass opacities | 0.7 | 415,927 |
| MR222✕✕ | 37 | Positive | Lymphoblastic lymphoma | Negtive | CLR/1M EMB/1M IMP/1M | EMB/2M IMP/2M | Multiple lung lesions with central cavitation | 0 | 838 |
| MR226✕✕ | 8 | Negative | Free | Negative | NA | NA | Multiple bilateral modular infiltrates, more in the left upper lobe | NA | N/A |
| MR244✕✕ | 28 | Positive | Pulmonary disease; hematologic disease | 2+ | CLR/1M RIF+INH/1M EMB/1M | MXF/4M | Multiple bilateral lung nodules; cavitation left lower lobe | 0.02 | 399,652 |
| MR246✕✕ | 17 | Negative | Pulmonary disease; chronic diarrhea | Negative | RIF/17M CLR/21M EMB/17M | NA | Left upper lobe consolidation | NA | N/A |
| MR1023✕✕ | 47 | Negative | DM; subclinical hypothyroidism | Negative | NA | NA | Bilateral nodular infiltrate; cavity, left upper lobe | NA | N/A |

The patient and sample data collected included demographic and clinical characteristics, age, sex, clinical features at presentation, and presence of co-morbid conditions including HIV infection and initial and modified therapy where applicable and outcome and antimicrobial susceptibility testing results. Once an isolate was suspected to be an NTM, the samples were sent out to reference laboratories for full identification and antimicrobial susceptibility testing. Radiographic and pathologic data were also captured. The use of antimicrobial agents before and after the isolation of M. riyadhense and immunosuppressive medications were documented, and the anti-TB drug regimens used with dosages and their respective durations were recorded (Table 1).

Culturing, DNA Isolation and Sequencing of Bacteria

The M. riyadhense strains were grown on Lowenstein Jensen (LJ) slants at 37° C. for two weeks, DNA was extracted using a phenol-chloroform protocol (Belisle and Sonnenberg, 1998) and the quality was measured by Qubit. The bacteria 20 µg of high-molecular weight (HMW) DNA from the 8 M. riyadhense strains was sequenced using the PacBio RSII sequencer (Pacific Biosciences, USA) with a 10 kb library. The NEBNext Ultra II DNA library preparation kit (New England BioLabs, UK) was used to prepare the libraries according to the manufacturer's instructions and sequences for each library using the Illumina HiSeq 4000 platform were generated for all M. riyadhense strains.

Genome Assembly and Annotation

The Illumina short reads were trimmed and low-quality reads were removed by Trimmomatic (Bolger et al., 2014). Eight consensus genomes based on each strain were assembled into contigs with the PacBio long reads using the Cairo assembler (Koren et al., 2017). After assembly, the draft genome was then corrected with short Illumina reads using the Pilon (Walker et al., 2014) software. Circularity of assemblies was checked by Gepard (Krumsiek et al., 2007) and assemblies were annotated by Prokka (Seemann, 2014). The circular map of the chromosome was compared with M. tuberculosis and visualized with BRIG (Alikhan et al., 2011). The genome of the MR226 strain was used as the high-quality reference in this work.

Comparison of Chromosomal and Plasmid Gene Contents in M. riyadhense to Various Mycobacterium Species DNA sequences of 152 Mycobacterium species and 77 mycobacterial plasmids were obtained from the NCBI genome database and independently annotated by Prokka (Seemann, 2014). The predicted protein sequences from the chromosome and each of the two plasmids (pMRLP01 and pMR01) of the M. riyadhense MR226 strain were then compared with the annotated genes from the rest of the mycobacteria species using orthoMCL (Li et al., 2003) with a 50% identity cut-off and the inflation parameter of 1.5. The obtained orthologs were visualized with the heatmap package in R (Ihaka and Gentleman, 1996). Focused OrthoMCL comparison was performed between (1) M. riyadhense, M. marinum, M. kansasii, M. szulgai and M. tuberculosis and (2) M. riyadhense and five species from the MTBC, namely: M. tuberculosis, Mycobacterium bovis, M. canettii, Mycobacterium mungi, Mycobacterium africanum.

SNPs Calling and Phylogeny Based on SNPs

The corrected Illumina reads were mapped using BWA (Li and Durbin, 2009) on to the MR226 genome assembly. Picard tools (Broad Institute, 2016) was used to clean the SAM files, fix the mate-pair information and mark the duplicates. SNPs were called for two iterations and filtered (QD<2.0, FS>60.0, SOQ>4.0, ReadPosRankSum<−8.0) with Genome Analysis Toolkit (GATK) (Alkan et al., 2011). The alignment file was generated by SVAMP (Naeem et al., 2014) and the phylogeny was generated by RaxML (Stamatakis et al., 2005) with the TVM model.

Phylogeny of M. riyadhense

The AMPHORA2 (Wu and Scott, 2012) pipeline was used to identify protein sequences from 31 conserved genes in the pangenome datasets and the *Mycobacterium* genomes available at NCBI or JGI up to 1 Jan. 2018. A total of 152 species were selected after applying a filter of at least 10 marker genes to be detected in each of the assemblies. *Nocardia abscessus* was used as the out-group. 12 genes, which have only one copy in each of the species (i.e. genes rplA, rplB, rplF, rplM, rplN, rplP, rplS, rplT, rpmA, rpsJ, rpsM, and rpsS), were concatenated, aligned and trimmed. The phylogenetic tree was then constructed using RaxML with Dayhoff model, which is calculated with a script provided in AMPHORA2 (Wu and Scott, 2012).

The whole genome phylogenetic tree was also performed with the MTBC species *M. tuberculosis, M. Bovis, M. canettii, M. mungi, M. orygis, M. africanum*) and with *M. kansasii, M. marinum, Mycobacterium shinjukuense, Mycobacterium leprae, M. smegmatis, Mycobacterium parmense, Mycobacterium avium* and *Mycobacterium abscessus*. The one-to-one orthologs of each species were obtained using OrthoMCL and concatenated, then aligned with Muscle (Edgar, 2004) and trimmed with TrimAL (Capella-Gutiérrez et al., 2009). The concatenated sequences were composed of 906 genes encoding 296,124 amino acids and were used to build a phylogenetic tree with LG+G+F model, which is selected by ModelGenerator. The phylogenetic tree was generated by RaxML (Stamatakis et al., 2005).

Toxin/Antitoxin, mce/mce-Associate Genes and ESX Systems in M. riyadhense and Other Mycobacteria The 158 Toxin/Antitoxin (T/A) proteins belonging to the VapBC, RelEF, HigBA, MazEF, ParDE and UCAT families were downloaded from NCBI protein database. *M. tuberculosis* T/A orthologs from all of the 152 species were identified by OrthoMCL (Li et al., 2003) and the ortholog groups were also examined by Blast+2.4.0. The same pipeline was also applied for the MCE family, PhoPR, PE/PPE, PE-PGRS, and ESX1-5.

Infection of RAW 246.7 Cell Line with M. riyadhense, M. kansasii and M. bovis BCG Denmark The murine macrophage RAW264.7 cell line obtained from American Type Culture Collection (ATCC, USA) was cultured in Dulbecco's modified Eagle's medium (DMEM) (ThermoFisher Scientific, USA) supplemented with 10% FCS, streptomycin, and penicillin. *M. riyadhense, M. kansasii* (subtype I), and *M. bovis* BCG Denmark strains were grown in Middlebrook 7H9 liquid medium after single colony isolation from LJ slants or 7H10 agar. 7H9 was supplemented with 10% albumin, dextrose and catalase (ADC) whilst 7H10 with oleic acid-albumin-dextrose catalase (OADC) in addition to 0.2% glycerol. Ready prepared LJ slants were provided by Saudi Prepared Media Laboratory (SPML, Saudi Arabia).

Before the infection, all bacterial cultures were centrifuged at 1000×g for 10 minutes. The supernatant was discarded and 10-15 3 mm glass beads were added to the pellet that was then vortexed for 1 minute in order to break it up. 6 ml of the DMEM culture media was then added to the pellet and left to rest for 5 minutes. The top 5 ml was then removed to a fresh 15 ml falcon tube, which was then centrifuged for a further 3 minutes at 200×g to remove remaining bacterial clumps. The supernatant was then taken and passaged using a 26G hypodermal syringe approximately 15 times to further break up any clumps of bacteria. The optical density of the culture was measured again before the infection experiment.

RAW264.7 cells were seeded at $2\times10^5$ cells per well in 24-well flat-bottom tissue culture plates 24 hours before to reach $5\times10^5$ cells per well. The DMEM over the cells was removed and the cells were washed 1 time with PBS. The cells were infected by applying 1 ml of DMEM media containing the mycobacteria prepared in former steps at appropriate concentration with MOI equals to 5, or DMEM alone for the control wells. The plates were then returned to the incubator at 37° C. with 5% $CO_2$ for 3 hours to allow for bacterial uptake by the RAW264.7 cells. The supernatant was removed after 3 hours, and the infected cells were washed with medium phosphate buffer saline (PBS) to remove extracellular bacteria. Subsequently, the cells were incubated in fresh DMEM medium with 10% TCS for 24 h and 48 h respectively. 400 µl of TRIzol (ThermoFisher Scientific, USA) was added to the wells, and the adherent cells were scraped out and stored at −80 C for RNA extraction. Each bacterial infection was performed in triplicates in addition to the non-infected controls. RNA was isolated from the samples using the Direct-zol™ RNA Miniprep kit (Zymo Research, USA) according to the manufactories' manual.

Agilent RNA 6000 Nano kit was used for checking quality and quantity of the total RNA. The murine nCounter Myeloid Innate Immunity Gene Expression Panel was used for this project. The obtained counts were normalised using the nSolver™ Advanced Analysis plugin (NanoString Technologies, USA) using the geNorm algorithm and differential gene (DE) expression was analyzed using multivariate linear regression in the nSolver™ software with 0.05 as the p-values cutoff.

Thin Layer Chromatography (TLC) Analysis of Lipooligosaccharide in M. riyadhense, M. kansasii, and M. marinum For the TLC analysis, bacterial strains were grown at 30° C. (*M. marinum*) or 37° C. (*M. smegmatis, M. kansasii, M. riyadhense*) on LJ slants and were collected and washed once with PBS. Apolar and polar lipids were extracted from the cell pellets using methods described by Dobson et al (G. Dobson. et al., 1985). Polar lipids were analyzed by 2D-TLC using solvent system E, which is designed to separate phospholipids and LOSs (G. Dobson. et al., 1985). Glycolipids were visualized by charring following staining with either molybdophophoric acid (MPA) or alpha-napthol (for glycolipids).

Development of Diagnostic Markers for *M. riyadhense*

To develop diagnostic markers for *M. riyadhense* for potential use in the clinical environments, unique regions within the *M. riyadhense* reference genome compared to 152 other mycobacteria species were detected using Shustring (Houold, et al., *BMC Bioinformatics* 2005; 6. DOI:10,1186/1471-2105-6-123). These regions were also examined by OrthoMCL (LI, et al., Genome Res., 12:2178-89 (2003) and Blastn (Camacho, et al., *BMC Bioinformatics* 2009; 10. DOI:10.1186/1471-2105-10-421). mr_00036, mr_00263, mr_00606, and mr_01005 genes were selected as the amplification targets.

Two primers for each gene were designed in this study:

```
                                          (SEQ ID NO: 1)
MRDP-MR_00036-F (5'-TTCGTTGTCGGTTTCGTCGC-3')
and (SEQ ID NO: 2)
MRDP-MR_00036-R (5'-GCGTCAGCTCCACCGAAAAC-3');

(SEQ ID NO: 3)
MRDP-MR_00263-F (5'-CCACCGCTGTTGGCGA-3')
and (SEQ ID NO: 4)
MRDP-MR_00263-R (5'- TTCGTCCCGTTGATCCCGTT -3');

(SEQ ID NO: 5)
MRDP-MR_00606-F (5'- AACCTGCCCGATACGCACTT -3')
and (SEQ ID NO: 6)
MRDP-MR_00606-R (5'- ACTGTTCCTCCGTGGGGTTG -3');

(SEQ ID NO: 7)
MRDP-MR_01005-F (5'- GACTGTGGGGTAACGGTGGA -3')
and (SEQ ID NO: 8)
MRDP-MR_01005-R (5'- CCGGTGATGTCGCCTACTCC -3');
```

The PCR was performed in a 25 μl reaction volume with 12.5 μl GoTaq® green master mix (ready to use 2×PCR solution containing Taq DNA polymerase, dNTPs, MgCL2 and reaction buffer at optional concentrations for efficient amplification of DNA templates by PCR) (Promega, USA), 1 μl of 100 ng/μl gDNA, 1 μl of 10 nmol of forward and reverse primer, 3 μl Dimethyl sulfoxide (DMSO) and 19 μl of nuclease-free water. The PCR mixture was denatured for 5 minutes at 94° C., followed by 35 cycles of amplification involving a denaturation step at 94° C. for 30 seconds, a primer annealing step at 59° C. for 45 seconds, a primer extension step at 72° C. for 45 seconds, and a final extension step at 72° C. for 7 minutes. The ITS-F/mycom-2 primer set (Park et al., 2000) which is a *Mycobacterium* genus-specific primer set was used as a control, with amplification conditions as described previously (Park et al., 2000). The products were electrophoresed in 2% agarose gels for 60 minutes and visualized.

Results

Clinical Characteristics

Between April 2011 and March 2017 eight clinical cases of infection due to *M. riyadhense* were recorded in patients aged 8 years and above (Table.1). The identified strains are MR193, MR206, MR210, MR222, MR226, MR244, MR246, and MR1023. All of the cases were males aged between 8 and 82; 3 were HIV positive, one had unknown HIV status, while the remaining 4 were HIV negative. They had a body mass index (BMI) value between 14.9 and 31.5. No consistent findings were observed while performing standard laboratory tests, ranging from complete blood count (CBC) and serum chemistry, except for persistent hypoalbuminemia and lymphopenia among the cases. In addition to HIV/AIDS, most of them had multiple co-morbidities such as pulmonary and/or systemic hypertension, malignancies, diabetes mellitus (DM), with the lung being the major site of disease (Table.1).

Microbiological Characteristics

Multiple respiratory samples from broncho alveolar lavage (BAL), endotracheal (ET), sputum, and lymph node samples were positive by culture from solid and liquid media using LJ agar and Mycobacteria growth indicator tube (MGIT) broth, respectively, with varying times to positivity. All samples were subjected to staining using AR (Auramine-rodamine stain) and ZN (Ziehl-Neelsen (stain) techniques (Table.1). The isolates were subjected to susceptibility testing for antibiotics commonly used to treat both typical and atypical infections. Isolates showed 100% susceptibility to, among others, rifampin (RIF), ethambutol (EMB), clarithromycin (CLR), rifabutin (RFB), linezolid (LZD), amikacin (AMK), moxifloxacin (MOXI), and trimethoprim-sulfamethoxazole (TMP-SMX). Three out of the eight isolates were resistant to ciprofloxacin (CIP). Although no consistent findings existed on chest imaging, most patients presented with upper lobe consolidation, cavitation, ground glass opacities and 'tree-in-bud' appearance, hilar lymphadenopathy and pleural effusion (FIG. 1). Two patients had multiple necrotic mediastinal and abdominal lymphadenopathy. Three out of four patients that had lymph node biopsy taken showed *M. riyadhense* infection, multiple epithelioid granulomas, multi-nucleated giant cells and necrosis and negative for malignancy.

Antimicrobial Therapy and Outcome

The earlier cases (MR244, MR206) were initially commenced on quadruple regular anti-TB regimens (RHEZ), but as new cases with similar characteristics continued to appear, the initial regimens were narrowed down to target NTM including clarithromycin and ethambutol. For the cases that started conventional regimens for antitubercular treatment (ATT) pending the final species identification and antimicrobial susceptibility, regimens were later narrowed down according to these results.

Assembly and Annotation of *M. riyadhense* MR226 Genome

The comparison of different assemblies of all sequenced *M. riyadhense* strains are listed in Table 2.

TABLE 2

Comparison of M. riyadhense strains' assemblies

|  | MR1023 | MR193 | MR206 | MR210 | MR222 | MR226 | MR244 | MR246 | Type strain assembly GCA_002101845.1 |
|---|---|---|---|---|---|---|---|---|---|
| Assembly Size (bp) | 6,906,827 | 6,695,517 | 6,835,855 | 6,528,955 | 6,533,138 | 6,888,178 | 6,775,970 | 6,916,580 | 6,269,850 |
| Chromosome size (bp) | 6,306,178 | 6,129,600 | 6,288,531 | 6,034,715 | 5,960,707 | 6,243,587 | 6,258,360 | 6,289,824 | 6,269,850 |
| Contigs | 9 | 7 | 6 | 2 | 7 | 3 | 9 | 4 | 263 |
| Gaps in chromosome | 0 | 0 | 0 | 0 | 0 | 0 | 0 | 0 | 262 |
| pMRLP01 | P | P | P | P | P | P | P | P | A |
| pMR01 | P | A | A | A | P | P | P | P | A |
| Transposase number in pMRL01 | 91 | 43 | 81 | 56 | 42 | 67 | 87 | 87 | 73 |
| CDS | 6185 | 5901 | 6124 | 5800 | 5852 | 6077 | 6030 | 6060 | 5,168 |
| Chromosomal CDS | 5630 | 5392 | 5634 | 5420 | 5353 | 5545 | 5637 | 5546 | 5,168 |

Chromosomes of all eight isolates in single contiguated sequences were obtained for a high-resolution genome comparison. The genome of M. riyadhense MR226 strain contains a 6,243,587 bp chromosome and a linear plasmid (pMRLP01) of 550,247 bp and a circular plasmid (pMR01) of 94,344 bp. The circular nature of the chromosome and the pMR01 plasmid were demonstrated through Gepard (Krumsiek et al., 2007).

As expected, owing to the free-living life style of this opportunistic pathogen, the chromosome of M. riyadhense is significantly larger than the chromosomes of the MTBC (data not shown).

The number of genes unique in a species showed that the members of the MTBC have considerably lower percentage of unique genes when compared with the M. riyadhense and other closely related NTMs (data not shown). The comparison of the annotated protein coding genes (CDS) from the MR226 strain to the genome assemblies of 152 mycobacterium species (including 77 known mycobacterial plasmids) shows that M. riyadhense has formed a close cluster with MTBC and few NTMs (data not shown). A total of 335 genes have been identified as unique genes from the ortholog groups comparison which are present only in M. riyadhense MR226, the vast majority of which belong to the PE/PPE family which are commonly believed to be involved in antigen variation and are widely spread across the slow-growing species within the Mycobacterium genus.

Linear plasmids were first described in 1989 in maize (which has a linear mitochondrion) (Leon et al., 1989) and have also been found in Actinomycetales such as Streptomycetes (Kinashi, 2011), Rhodococcus (Crespi et al., 1992) and Mycobacterium species, such as Mycobacterium xenopi, Mycobacterium branderi and Mycobacterium celatum. They are often accompanied by a circular plasmid in the same host (Picardeau and Vincent, 1997). The linear plasmid pMRLP01 contains a pair of partitioning genes (parA/parB) which are involved in active segregation and thus stabilize the inheritance of the plasmid (Surtees and Funnell, 2003). The latter are known to contribute to genome evolution by active DNA transfer and exchange (Zrimec and Lapanje, 2018). As is often the case for large plasmids, both circular and linear, a relatively high proportion of pMRLP01 genes (51%) show no significant database matches compared to the main chromosome (26%). This reinforces the idea that plasmids are an important route by which new genes are introduced to the genome in Mycobacteria. Of the 443 predicted protein coding genes (CDs features) of pMRLP01, 118 have at least one ortholog in the main chromosome. Furthermore, we observed several CDs in pMRLP01 that have orthologs in the genomes of Mycobacterium tusciae JS617, Mycobacterium aromaticivorans JCM 16368, Mycobacterium llatzerense, Mycobacterium obuense, Mycobacterium novocastrense and Mycobacterium holsaticum (data not shown).

In this study, we have further identified a circular plasmid termed pMR01 in M. riyadhense (data not shown). When compared with the circular plasmids of other species, such as pRAW in M. marinum (Ummels et al., 2014), pMAH135 (Uchiya et al., 2015) and pMA100 (da Silva Rabello et al., 2012) of Mycobacterium avium, pMyongI from Mycobacterium yongonense (Kim et al., 2013), pMK12478 (Veyrier et al., 2009) from M. kansasii and several plasmids from Mycobacterium chimera (van Ingen et al., 2017), a strong similarity was observed. These plasmids all harbor both a Type IV (TS4) and a Type VII (TS7) secretion system, which are necessary for conjugation (Morgado et al., 2017). Their presence facilitates the exchange of genetic material between different species of slow-growing mycobacteria (Ummels et al., 2014). This observation suggests that pMR01 is a novel conjugative plasmid.

A total of five Type VII secretion systems have been described to date, named ESX-1 to ESX-5[5,6]. An esx-5 locus on pMR01, which shows a high similarity to the ESX-5 loci on pMK12478, pRAW and pMAH135, is markedly different from the ESX-5 system found on the main M. riyadhense chromosome. ESX-5 is linked to M. tuberculosis pathogenicity and is involved in modulating the host immune responses to maintain a persistent infection (Weerdenburg et al., 2012). The potential transmissibility of pMR01 and other pMR01-like plasmids may mediate the evolution of the ESX systems in mycobacteria.

The progressive alignments of the assembled chromosomes and plasmids of each M. riyadhense strains show the chromosomes are relatively conserved (data not shown); the linear plasmids that are present in all of 8 isolates, are quite diverse from both structure and similarity perspective, and the pRAW-like plasmids are only present in MR226, MR193 and MR222 strains.

The SNP-based phylogeny of the sequenced M. riyadhense isolates indicates presence of two different Glades of M. riyadhense (data not shown). The nucleotide diversity between the MR222 clades is greater than the M. tuberculosis strains (Jia et al., 2017) while smaller than the *M. canettii* strains (Supply et al., 2013), and the variation between the MR226 clades is comparable to the SNP's variation in MTB strains.

Regions of Difference in *M. riyadhense*

The regions of difference (RD) were originally described as a genomic region present in virulent *M. bovis* and *M. tuberculosis* but absent from the *M. bovis* BCG genome. RD loci show independent deletion across MTBC members, and contain genetic functions believed to contribute to pathogenicity (Jakko Van Ingen et al., 2009) (Kozak et al., 2011) (Ru et al., 2017) and evolution of MTBC members (Brosch et al., 2002). *M. riyadhense* MR226 was found to harbor most of the RD loci (RD1, RD3-R11, R13-RD16) that are also intact in *M. tuberculosis*, while 2 of the RDs, RD2$^{riyadh}$ (data not shown) and RD12$^{riyadh}$ (data not shown)) show unique deletions. This deletion was also observed in other *M. riyadhense* strains as well.

Disruption of RD2 in *M. tuberculosis* led to decreased proliferation and impaired modulation of the host innate immune response (Kozak et al., 2011). The RD2 region (rv1978~rv1988, 2,220,725~2,231,846) is absent in *M. riyadhense* and RD2$^{riyadh}$ shows a bigger deletion (2,216, 498~2,246766) which contain 29 genes (rv1971~rv2000), while 8 genes within this locus (rv1978, rv1979c, rv1980c, rv1981c, rv1983, rv1984, rv1987, rv1988) have orthologs in different locations in genome of *M. riyadhense* (mr_05764, mr_05852, mr_02310, mr_02993, mr_00486, mr_02995, mr_02325, mr_02349, mr_01747).

RD12 is deleted in the vaccine *M. bovis* BCG strains, *M. bovis, M. caprae* and *M. orygis* (Alexander et al., 2010) but present in other MTBC members. *M. canettii* isolates (except group B (M Cristina et al., 2005)) also show an independent deletion at the RD12 locus named RD12$^{can}$ (3,479,430~3,491,866, rv3111~rv3126) which is different from the RD12 (3,484,740~3,487,515, rv3117~rv3121). The unique deletion at the RD12 locus found in *M. riyadhense* was designated as RD12$^{riyadh}$ as it encompasses a larger deleted region from rv3108-rv3127 (3,477,171~3,492,150) (data not shown)) compared with RD$^{can}$ and RD12 which confirm the independence of this deletion event. This deletion is present in all the isolates of *M. riyadhense* and it is specific to *M. riyadhense*.

Comparative Phylogeny of *M. riyadhense* with Other Mycobacteria

The phylogenetic tree based on 12 marker genes shows that the slow-growers and rapid growers are separated into two different clades and that fast-evolved from slow-growers (data not shown) and the overall topology was remarkably similar to previously published phylogenetic trees (Tortoli et al., 2017). In the tree *M. riyadhense* is located within the same clade as the causal organisms of most of the mycobacterial diseases in humans that includes the MTBC, *M. marinum, M. kansasii, M. leprae* and other related host-restricted mycobacteria with reduced genome sizes and decreased survivability in the environment. *M. shinjukuense* and *M. lacus* and *M. riyadhense* forms a sub-clade which is phylogenetically close to MTBC.

The PE/PPE family genes, mce and mce-associated genes are known to be of importance for host adaptation (Delogu and Brennan, 2001) and pathogenicity (Isom et al., 2017). The PE/PPE family genes are enriched in the MTBC members, *M. riyadhense* MR226 (278) and other pathogenic species such *M. kansasii* (228) and *M. ulcerans* (200). The number of mce or mce-associated genes has not significantly changed across mycobacterial genomes, indicating that this group of genes play functional roles bridging both environmental and obligate pathogen lifestyles. A comparative phylogenetic map based on 1,301 conserved proteins reveals this downsizing of the genome, and the dynamic changes in genome components (data not shown). Certain functional categories of genes are relatively enriched during evolution of MTBC including protein metabolism, regulation and cell signaling, cell division and cell cycle. The number of genes related to core metabolic functions such as metabolism of aromatic compounds and genes associated with secondary metabolism have been reduced in the *M. riyadhense* genome and in the MTBC members indicating adaptation to the intracellular environment.

Figure 2A:
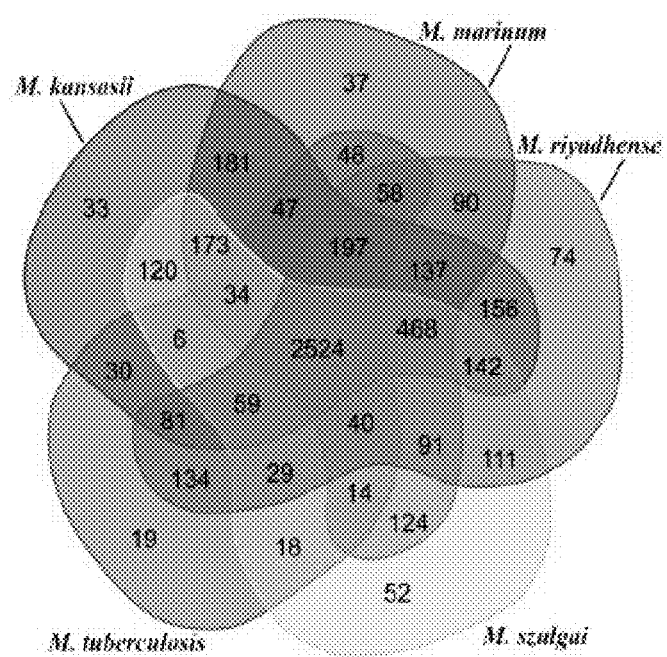

*M. riyadhense* shares a larger number of orthologs (3,122) with *M. tuberculosis* compared to *M. kansasii* (2,978), *M. marinum* (2,962) and *M. szulgai* (2,724) among the environmental mycobacteria closely related to the MTBC (FIG. 2A). A total of 134 orthologs were exclusively shared between *M. riyadhense* and *M. tuberculosis* compared with the number of orthologs exclusively shared between *M. tuberculosis* and *M. kansasii* (30), *M. marinum* (48) and *M. szulgai* (18), respectively (FIG. 2A). It was notable that genes from the phage-derived regions of RD3 and RD11 were shared exclusively between *M. riyadhense* and *M. tuberculosis*.

Figure 2B:
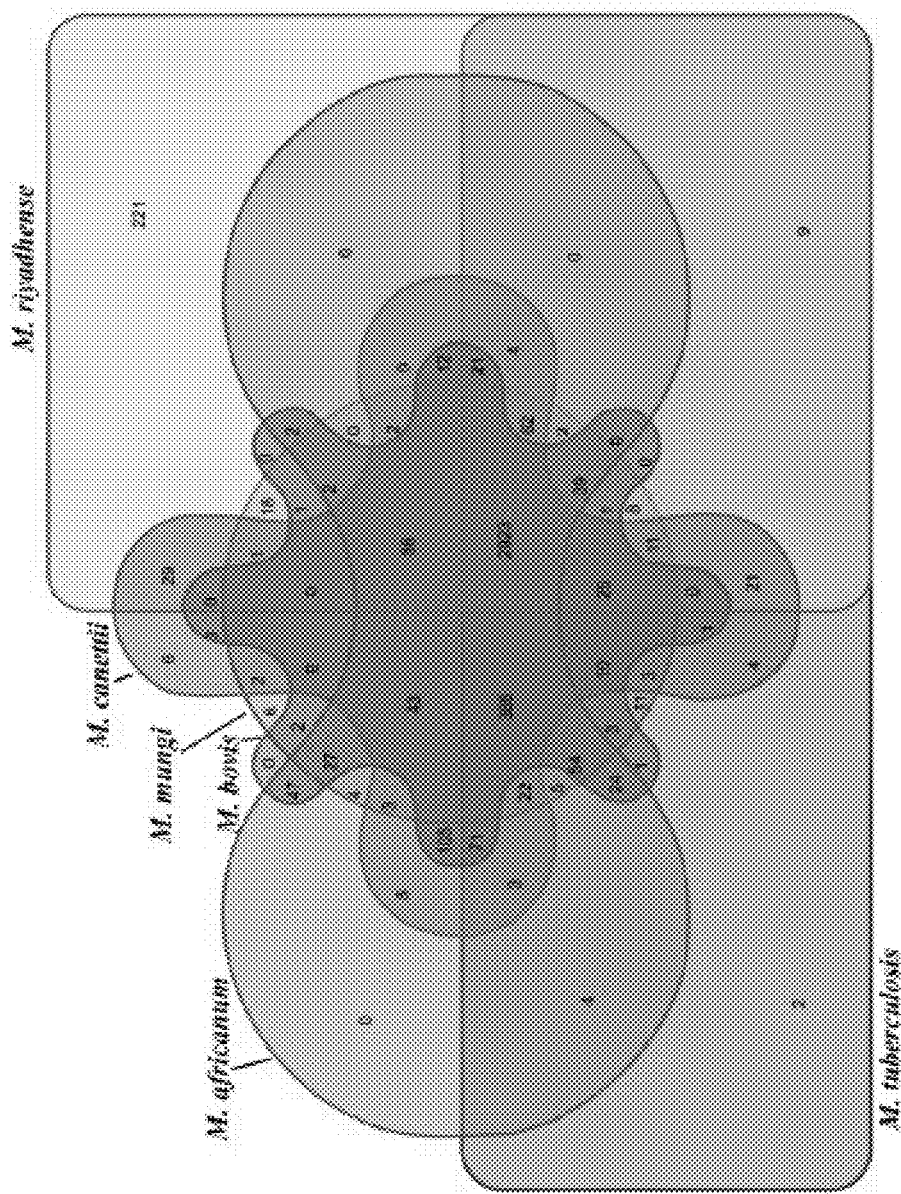

When comparing the ortholog groups of *M. riyadhense* and MTBC members, 385 ortholog groups which are not present in *M. riyadhense* but present exclusively in MTBC members, while *M. riyadhense* contains a large number of orthologs (221) which are not present among the MTBC members (FIG. 2B). This likely illustrates the constraints imposed by the free-living lifestyle of *M. riyadhense* that maintains a broad functional repertoire to secure environmental survival while the obligate pathogens of the MTBC have lost genes involved in environmental survival and gained a large number of genes required for persistence in the host.

The toxin and antitoxin systems (T/A) were first found on plasmids or plasmid-derived chromosomal loci to promote plasmid maintenance in bacterial populations (Cooper and Heinemann, 2000). The hallmark of *M. tuberculosis* is the ability to survive long-term in the host granulomas and develop a latent stage. The molecular mechanisms and the cellular components that are involved in the persistence of *M. tuberculosis* are still poorly understood, but several T/A have been implicated in the pathogenicity of *M. tuberculosis* (Slayden et al., 2018). The 79 pairs of T/A (HigAB, MazEF, ParDE, RelEF, VapBC and UCAT) in *M. tuberculosis* were compared with the T/A pairs found in other members of the MTBC and NTMs. Based on presence of the 49 out of the 79 T/A ortholog pairs (data not shown), *M. riyadhense* appear as more closely related to the MTBC members compared with other mycobacteria including *M. lacus, M. shinjukuense* and *M. decipiens*; the shared T/A pairs may play a role in pathogenicity or persistence of *M. riyadhense* infection in a similar functional way to those in *M. tuberculosis*.

*M. riyadhense* Strains Produce a Distinct Pattern of LOSs

Lipooligosaccharides (LOS) genes have previously been linked to colony morphology, secretion of PE/PPE family proteins, and the pathogenicity of *M. marinum* (Van Der Woude et al., 2012). They are also produced by other mycobacteria including *M. kansasii* and the 'smooth TB' strain *M. canettii*. The wecE and galE6 LOS genes are absent from the *M. riyadhense* genome.

Figure 3A:
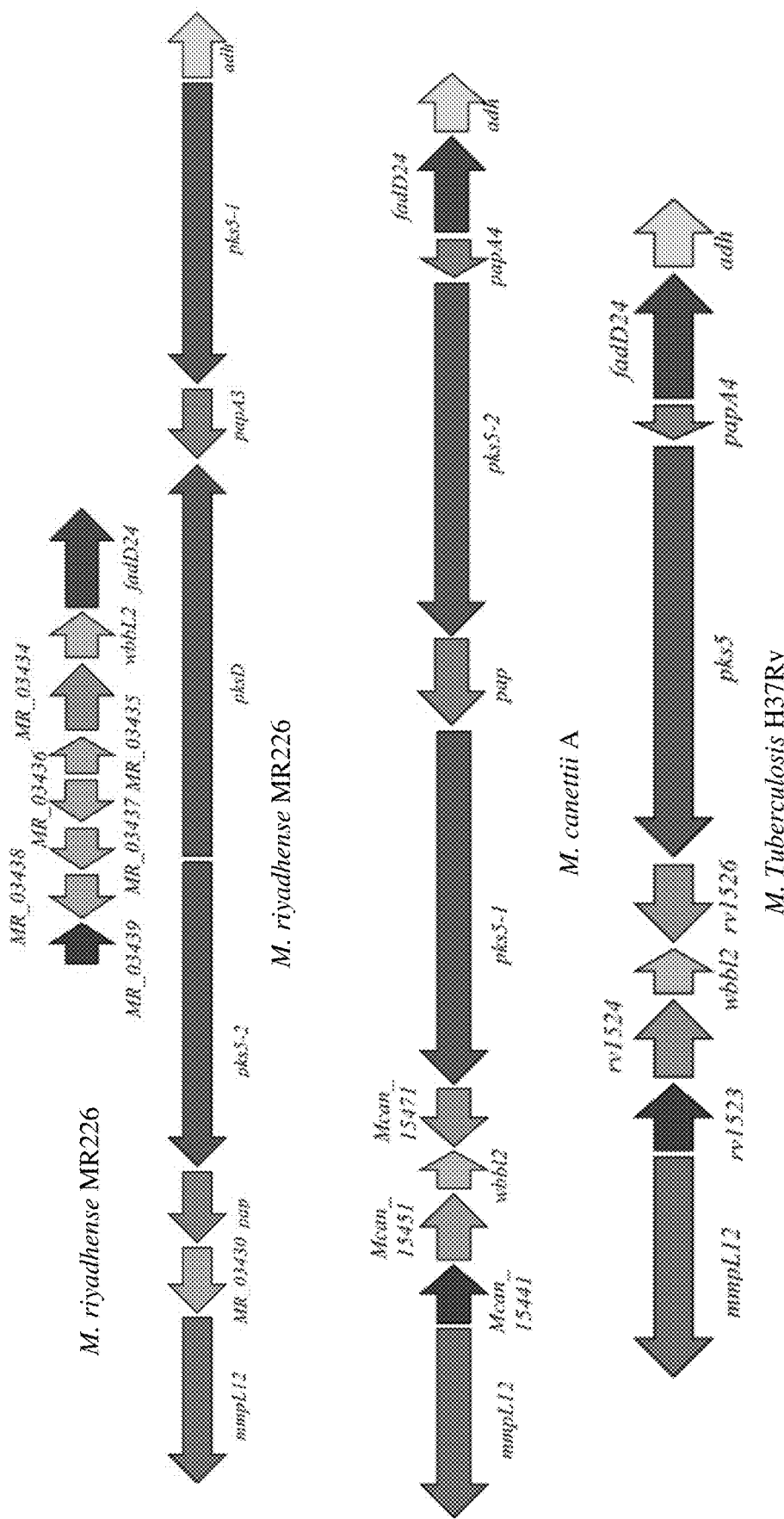

These genes are linked with the removal of LOS-II* and the production of LOS IV (Van Der Woude et al., 2012). Thus, their absence is likely to cause an accumulation of LOS-II* and the lack of fully formed LOS IV, which have previously been shown to increase the pathogenicity in *M. marinum* (Van Der Woude et al., 2012). Furthermore, both the pks5 and pap genes in the LOS locus are intact in *M. riyadhense*, as is the case in *M. canettii*, but not in *M. tuberculosis*, where the former is truncated, while the latter has been deleted (Boritsch et al., 2016). This indicates that that pks5 recombination and pap deletion occurred in a common ancestor of the MTBC after its differentiation from both *M. riyadhense* and *M. canettii*. Noticeably, the arrangement of the LOS gene locus in *M. riyadhense* is quite different from *M. canettii, M. tuberculosis, M. kansasii* and *M. marinum* and some rearrangement of the locus have occurred exclusively in *M. riyadhense* (FIG. 3A).

Figure 3B:
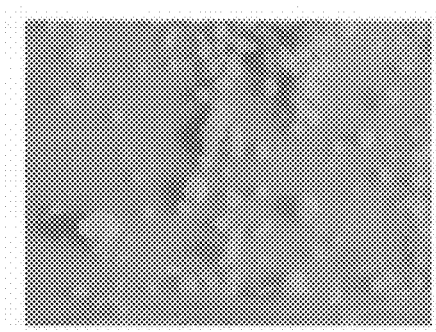
Figure 3C:
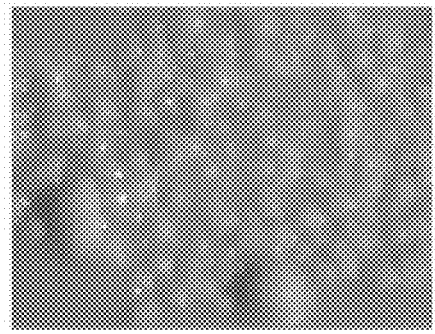
Figure 3D:
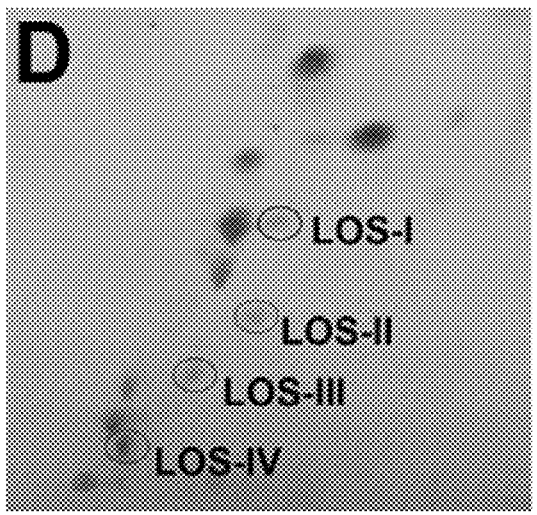
Figure 3E:
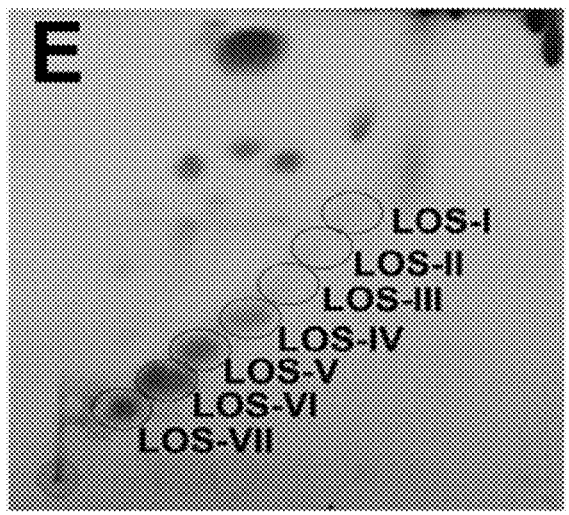
Figure 3F:
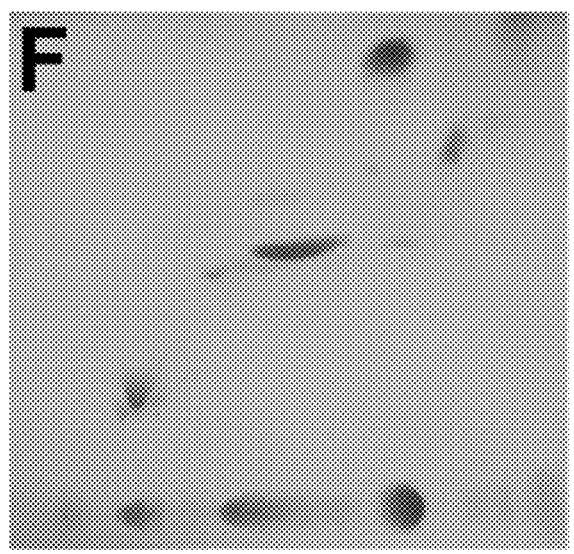
Figure 3G:
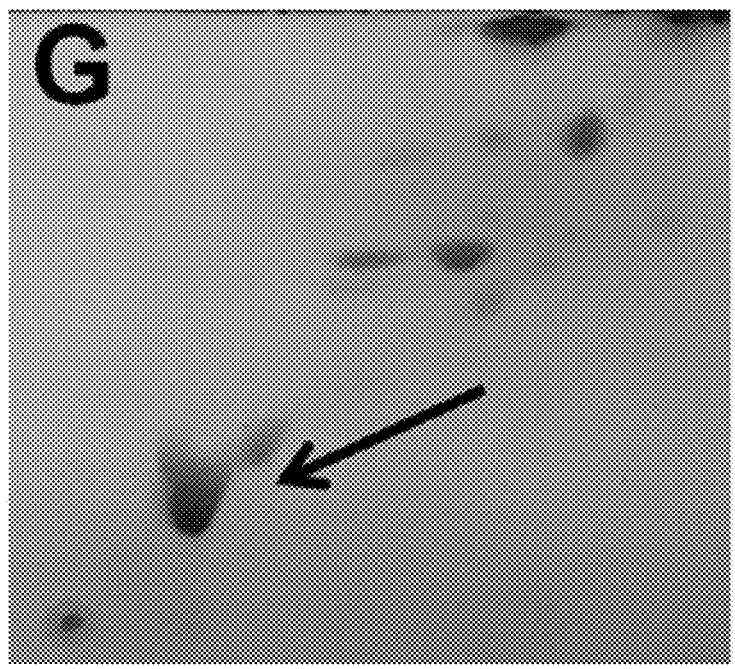
Figure 3H:
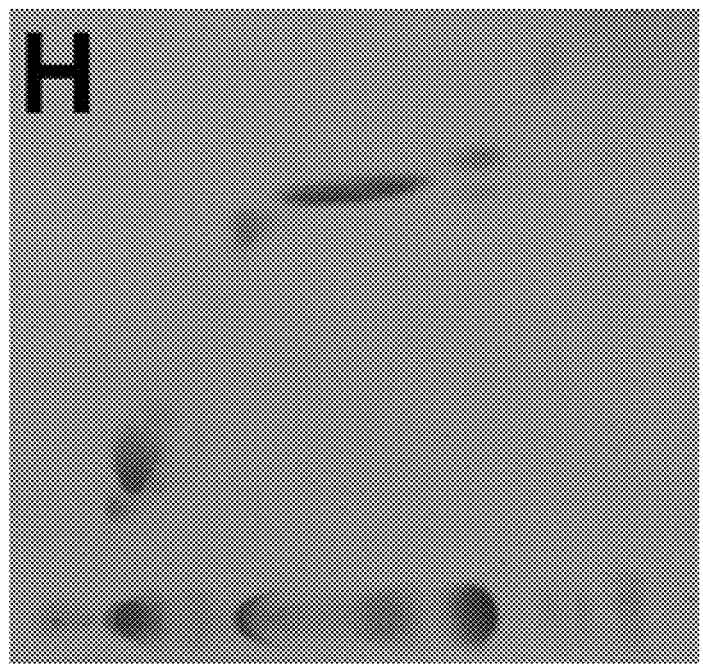
Figure 3I:
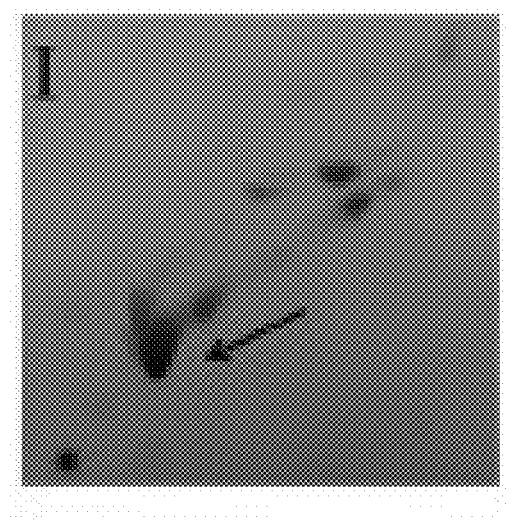

We have observed both smooth (MR210, MR222, MR226, MR244, MR246, MR1023) (FIG. 3B) and rough (MR193 and MR206) (FIG. 3C) morphology in these strains. To correlate colony morphology with LOS production, we extracted polar lipids from the strain and analyzed them by 2D-TLC using solvent system E (G. Dobson. et al., 1985), which is designed to separate phospholipids and LOSs. Charring of the TLC plates with alpha-naphthol revealed glycolipids, including the accumulation of a species that migrated at a position similar to that of LOS III. This lipid was seen only in smooth strains, and species with migration patterns to similar to LOS I and LOS II were observed, while LOS IV was absent. This was not unexpected as all *M. riyadhense* strains lack a functional wecA gene which is required for the extension of LOS II to LOS IV (FIG. 3A). Additionally, the relative levels of the predominant LOS species seem to be quite high when compared to those seen in other LOS-producing mycobacteria (FIG. 3 (D)(E)). The rough strains on the other hand did not produce any glycolipids that migrated in the positions corresponding to LOSs (FIG. 3 (F)(H)). Overall, *M. riyadhense* seems to exhibit a LOS production phenotype distinct from other LOS producing mycobacteria.

PE-PGRS33 Locus and Type VII Secretion System of *M. riyadhense*

Figure 4:
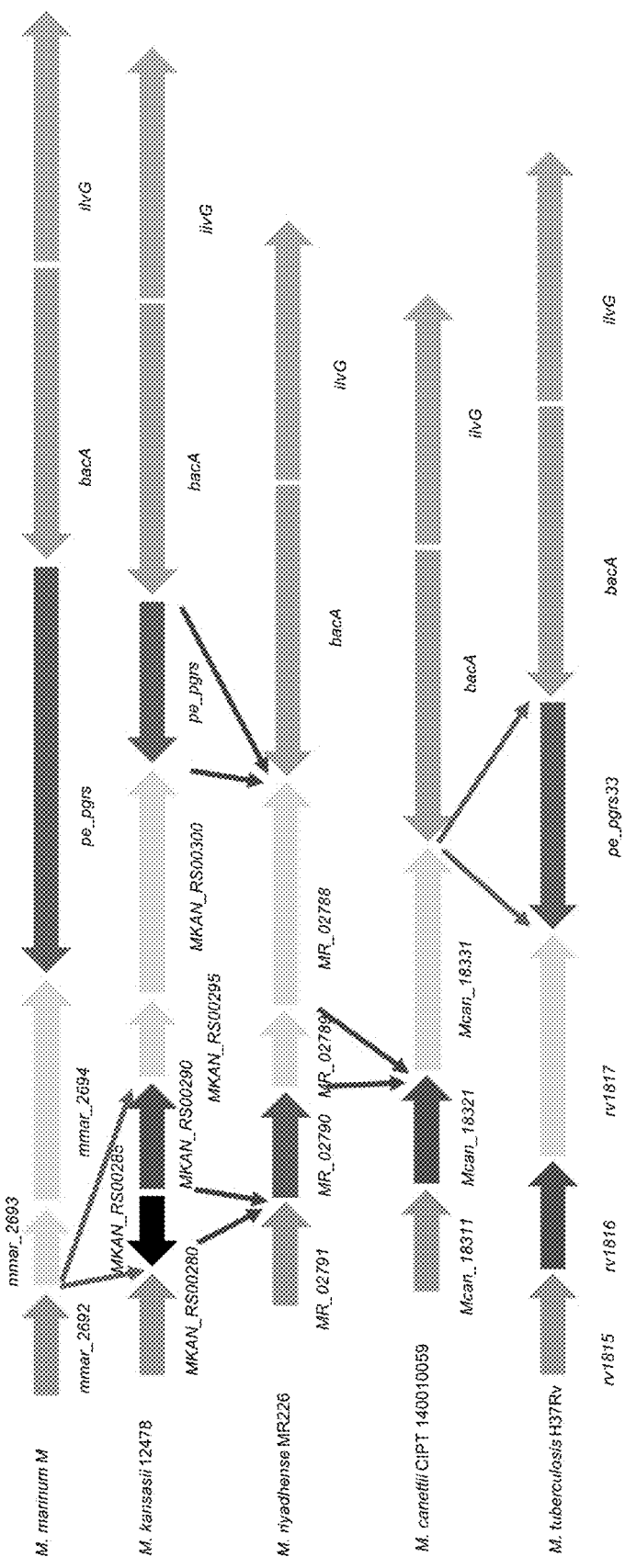

The pe-pgrs33 (rv1818c) locus encodes the exported protein PE_PGRS33 and plays an important role in the pathogenesis of *M. tuberculosis* (Cohen et al., 2014). A previous study (Boritsch et al., 2014) showed that pe-pgrs33 is present in all MTBC members but not in *M. canettii*, which implies a specific pe_pgrs33 insertion event in the ancestor of MTBC strains. Genome comparison of *M. riyadhense* and *M. tuberculosis, M. kansasii, M. marinum* and *M. canettii* provides additional evidence that *M. riyadhense* is the missing link of pe-pgrs33 deletion/insertion event. Our phylogeny strongly suggests that the deletion of the pe-pgrs33 from *M. kansasii* and *M. marinum* happened before the divergence of environmental mycobacteria and the smooth tubercle bacilli (STB)/MTBC clade (FIG. 4).

Figure 5:
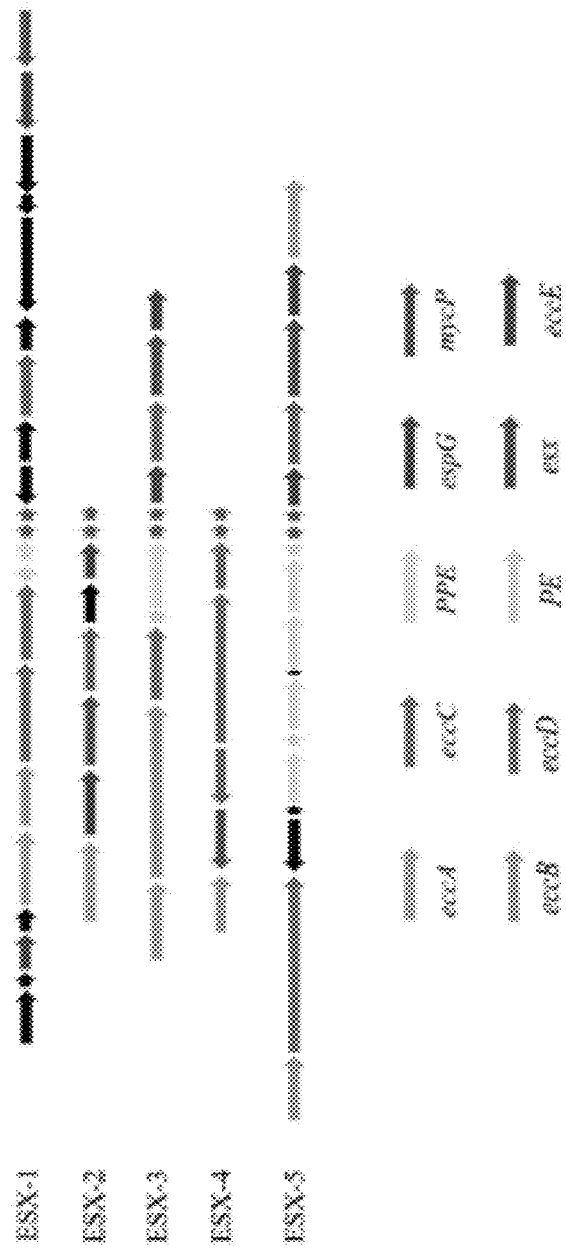

All of the 5 ESX systems (ESX1-ESX5) were found in the *M. riyadhense* genome (FIG. 5).The eccA and eccB genes are absent from the ESX-2 system. The espACD operon, which has been reported as important for the pathogenicity of *M. tuberculosis* and secretion via ESX1 is also missing in *M. riyadhense*. The overall gene arrangement of the ESX1-ESX5 loci is very similar in both *M. riyadhense* and in *M. tuberculosis* (Houben et al., 2014). This conserved synteny reinforces the previous results that phylogenetically *M. riyadhense* may represent an ancestral state to *M. canettii* and the MTBC. As noted before, the pMR01 plasmid also contains an extra ESX-5 locus, which could indicate a role of the plasmid in mediating pathogenicity.

Transcriptional Response of Murine Macrophage Cell Upon *M. riyadhense* Infection Our genomic analysis of *M. riyadhense* had revealed a range of genes and potential systems that could play a role host pathogen interaction. One such locus was orthologous to the ESX-1 secretion system that has been implicated in the ability of *M. tuberculosis* to avoid the antibacterial systems of the macrophage. Studies were conducted to assess the initial interaction of *M. riyadhense* with macrophages, using the RAW264.7 murine cell line as the experimental model. As comparator strains in these analyses, parallel infections with *M. kansasii*, an opportunistic pathogen that also contains an orthologous ESX-1 system, and *M. bovis* BCG, the live TB vaccine that is attenuated through deletion of the ESX-1 system, were also performed.

RNA was harvested from infected macrophages and uninfected controls at 3, 24 and 48 hours. To analyze complex immune responses of macrophage, the transcriptional response of the macrophages was analyzed using a 754 probe Nanostring Murine Myeloid Innate Immunity panel V2 (Kumar et al., 2017). Analysis of the resulting gene expression profiles showed that the overall response to infection with *M. riyadhense* and *M. kansasii* trigged more similar macrophage transcriptional responses than compared to BCG infection (data not shown). These analyses revealed an expected commonality in the responses, such as induction of proinflammatory genes through TLR signaling across all three infections (e.g. upregulation of IL1B, TNFA, CCL4, PTGS2 and CXCL2, albeit to different absolute levels). Distinct responses triggered by BCG infection as compared to *M. riyadhense* and *M. kansasii* included for example upregulation of MARCO in BCG (data not shown); MARCO is involved in pathogen uptake via trehalose dimycolate, a lipid that is known to show variation in structure between MTBC and *M. kansasii* (Bowdish et al., 2009) (Fujita et al., 2005). CCL24 and CXCL14, involved in attraction of immune cells to the site of infection (Stavrum et al., 2011), were upregulated to higher levels in *M. riyadhense* and *M. kansasii* compared to BCG at 24 and 48 hours.

Developing a Rapid PCR-Based Diagnostic Marker for *M. riyadhense*

Due to the issues previously encountered in diagnosing *M. riyadhense* infections (van Ingen et al., 2009) (Choi et al., 2012), correctly identifying cases of *M. riyadhense* infection early upon presentation at the healthcare units is of paramount importance.

By identifying unique K-mers ranging in size from 11 bp to 4209 bp in the assembled genome compared to the genomes of 152 other mycobacterial species, a primer set was developed targeting the mr_00263, mr_00606, and mr_01005 genes. The MRDP primer pair MRDP-F/MRDP-R amplified a single product of 372 bp from each of the eight isolates of *M. riyadhense* (FIG. 6) but not from other Mycobacteria species including *M. tuberculosis, M.*

Figure 6:
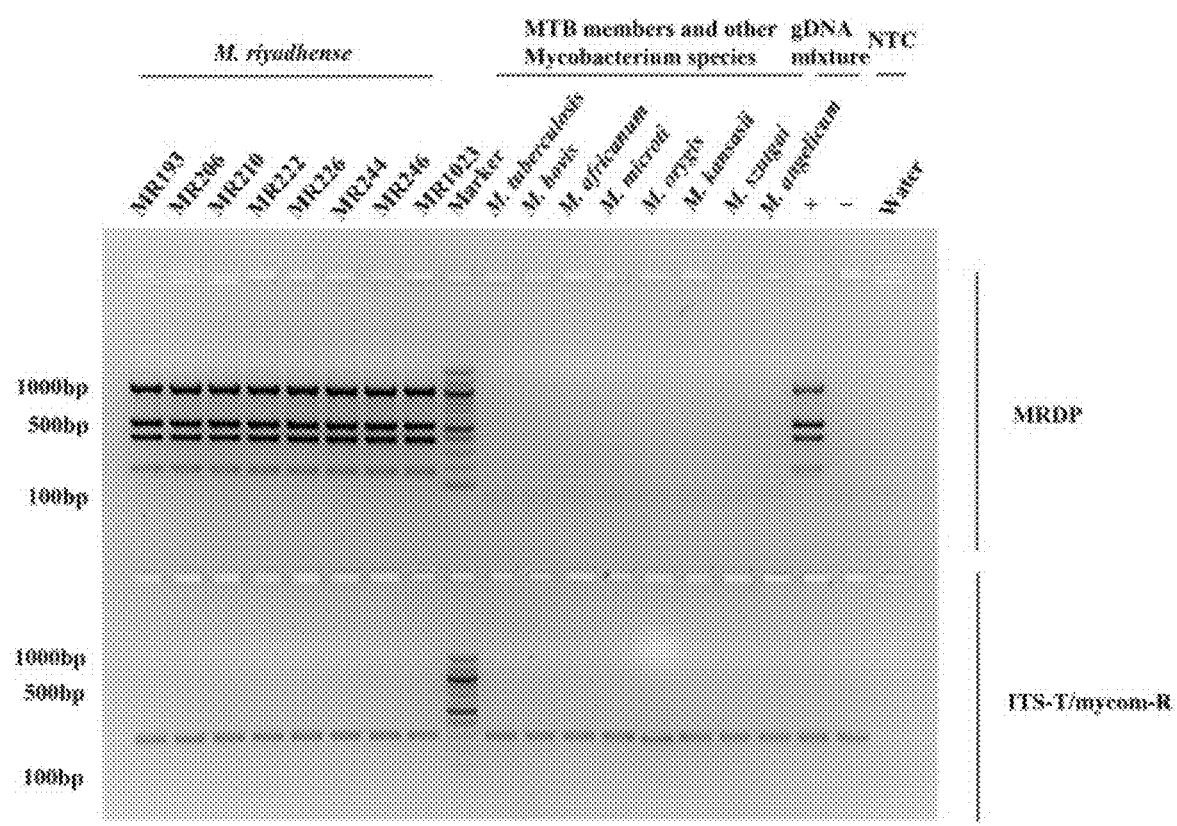

*bovis, M. kansasii, M. szulgai, M. avium* and *Mycobacterium angelicum*. The amplicon sizes for each pair of the gene sets are: MR_00036, 372 bp; MR_00263, 994 bp; MR_00606, 166 bp; and MR_01005, 511 bp, and these were present in each of the eight *M. riyadhense* isolates, but not in other Mycobacteria species (FIG. 6).

This shows that the MRDP-F/MRDP-R primers are highly specific to *M. riyadhense*.

Discussion

Due to the relatively recent emergence of *M. riyadhense* as an opportunistic human pathogen and its misdiagnosis by commercially available detection kits, an accurate set of diagnostic markers based on the genomic datasets generated in this study. The primer sets accurately diagnose *M. riyadhense* in a mixed cocktail of closely related mycobacteria and serve as part of an accurate and fast diagnostic protocol in a clinical setting. These primers could also serve as a tool for a global survey of cases of *M. riyadhense* infections that may be generally overlooked and thus may provide a more complete picture of the true extent of opportunistic human infections with this species. It would, for example, be of clinical interest to see if cases of *M. riyadhense* infections occur in Africa and South America, for which no reports are available, or if *M. riyadhense* is a local phenomenon concentrated in the Arab peninsula. The natural environmental reservoir of *M. riyadhense* is yet to be discovered. Systematic screening of relevant environmental samples with the MRDP established in this study may help to establish the natural environmental habitats for *M. riyadhense*. In conclusion, these provides unprecedented insights into ancestry and adaptive evolution in the MTBC in relation to other related NTM species and projects *M. riyadhense* as one of the closest environmental relatives and experimental model to study mycobacterial evolution and pathogenesis of the MTBC complex.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

1. Falkinham. *Semin Respir Crit Care Med* 2013; 34: 95-102.
2. Van Ingen, et al. *Thorax* 2009; 64: 502-6.
3. Ding et al. *J Formos Med Assoc* 2005; 104: 897-904.
4. Panwalker et al. *Infect Control* 1986; 7: 67-70.
5. Carbonne et al. *J Clin Microbial* 2009; 47: 1961-4.
6. Singh et al. *Open Forum Infect Dis* 2018; 5: S29-S29.
7. Garbati, Hakawi A M. *Mycobacterium riyadhense* Lung Infection in a Patient with HIV/AIDS. 2014 ttp:/www.s-sajm.org/article.asp?issn=2384-5147;year=2014;volume=1;issue=1;spage=56;epage=58;aulast=Garbati.
8. Choi et al. *Ann Lab Med* 2012; 32: 298-303.
9. van Ingen J et al. *Int J Syst Evol Microbial* 2009; 59: 1049-53.
10. King et al. *PLoS One* 2017; 12. DOI:10.1371/journal.pone.0173811.
11. Narendrula-Kotha R, et al. *PLoS One* 2017; 12. DOI: 10.1371/journal.pone.01168497.
12. Godreuil et al. *Emerg. Infect. Dis.* 2012; 18: 176-8.
13. Van der Werf et al. *BMC Infect Dis* 2014; 14. DOI: 10.1186/1471-2334-14-62.
14. Althawadi et al. *Mycobacterium riyadhense*. 2017; 23: 2015-7.
15. Tortoli et al. *J. Clin. Microbial*. 2010; 48: 307-10.
16. Van Soolingen et al., *Int J Syst Bacterial* 1997; 47: 1236-45.
17. Blouin et al. *PLoS One* 2012; 7: e52841.
18. Murty *Mycobact Dis* 2014; 4. DOI:10.4172/2161-1068.1000172.
19. Jang et al. *Trends Microbiol* 2008; 16: 303-8.
20. Wang et al. *Genome Biol Evol* 2015; 7: 856-70.
21. Stinear et al. *Genome Res* 2008; 18: 729-41.
22. Tortoli et al. *Infect Genet Evol* 2017; 56: 19-25.
23. Brown-Elliott et al. *Int J Syst Evol Microbial* 2018; 68: 3557-62.
24. Saito et al. *Int J Syst Evol Microbial* 2011; 61: 1927-32.
25. Fedrizzi et al. *Sci Rep* 2017; 7. DOI:10.1038/srep45258.
26. Belisle et al. *Methods Mol Biol* 1998; 101: 31-44.
27. Bolger et al. *Bioinformatics* 2014; 30: 2114-20.
28. Koren et al. *Genome Res* 2017; 27: 722-36.
29. Walker et al. *PLoS One* 2014; 9. DOI:10.1371/journal.pone.0112963.
30. Krumsiek et al. *Bioinformatics* 2007; 23: 1026-8.
31. Seemann, *Bioinformatics* 2014; 30: 2068-9.
32. Alikhan al. *BMC Genomics* 2011; 12. DOI:10.1186/1471-2164-12-402.
33. Li, et al. *Genome Res* 2003; 13: 2178-89.
34. Ihaka R, G al. *J Comput Graph Stat* 1996; 5: 299-314.
35. Li et al. *Bioinformatics* 2009; 25: 1754-60.
36. Broad Institute. Picard tools. https://broadinstitute.github-b.io/picard/.2016. https://broadinstitute.github.io/picard/%5Cnhttp://broadinstitute.github.io/picard/.
37. Alkan, et al. *Nat Rev Genet* 2011; 12: 363-76.
38. Naeem, el al. *Bioinformatics* 2014; 30: 2227-9.
39. Stamatakis, et al. *Bioinformatics* 2005; 21: 456-63.
40. Wu, et al. *Bioinformatics* 2012; 28: 1033-4.
41. Edgar, *BMC Bioinformatics* 2004; 5: 113.
42. Capella-Gutiérrez, et al *Bioinformatics* 2009; 25: 1972-3.
43. Dobson, et al. Systematic analysis of complex mycobacterial lipids. In: Chemical Methods in Bacterial Systematics. Academic Press, London, United Kingdom, 1985: 237-65.
44. Haubold, et al. *BMC Bioinformatics* 2005; 6. DOI: 10.1186/1471-2105-6-123.
45. Camacho, et al., *BMC Bioinformatics* 2009; 10. DOI: 10.1186/1471-2105 10-421.
46. Park H, et al. *J Clin. Microbiol* 2000; 38: 4080-5.
47. Huerta-Cepas J, et al. *Nucleic Acids Res* 2016; 44: D286-93.
48. Leon P, et al. *Nucleic Acids Res* 1989; 17: 4089-99.
49. Kinashi H. J. Antibiot. (Tokyo). 2011; 64: 19-25.
50. Crespi M, et al. *EMBO J* 1992; 11: 795-804.
51. Picardeau M, et al. *J Bacteriol* 1997; 179: 2753-6.
52. Surtees J A, et al. *Curr Top Dev Biol* 2003; 56: 145-80.
53. Zrimec J, et al. *Sci Rep* 2018; 8. DOI:10.1038/s41598-018-20157-y.
54. Ummels R, et al. *MBio* 2014; 5. DOI:10.11.28/mBio.01744-14.
55. Uchiya K I, T et al. *PLoS One* 2015; 10. DOI:10.1371/journal.pone.01117797.
56. da Silva Rabello M C, et al. *PLoS One* 2012; 7. DOI:10.1371/journal.pone.0029884.

57. Kim B-J, et al. *Genome Announc* 2013; 1: 604-13.
58. Veyrier F, et al. *BMC Evol Biol.* 2009; 9. DOI:10.1186/1471-2148-9-196.
59. van Ingen et al. *Lancet Infect Dis* 2017; 17: 1033-41.
60. Morgado S M, et al. *Mem Inst Oswaldo Cruz* 2017; 112: 514-6.
61. Abdallah A, et al. *Nat Rev Microbiol* 2007; 5: 883-91.
62. Weerdenburg E M, et al. *Cell Microbiol* 2012; 14: 728-39.
63. Jia X, et al. *Front Cell Infect Microbiol* 2017; 7. DOI:10.3389/fcimb.2017.00088.
64. Supply P, et al. *Nat Genet* 2013; 45: 172-9.
65. Van Ingen J, et al. *J Bacteriol* 2009; 191: 5865-7.
66. Kozak R A, et al. *Infect Immun* 2011; 79: 59-66.
67. Ru H, et al. *Front Cell Infect Microbiol* 2017; 7. DOI:10.3389/fcimb.2017.00239.
68. Brosch R, Gordon S V., Marmiesse M, et al. A new evolutionary scenario for the *Mycobacterium tuberculosis* complex. *Proc Natl Acad Sci* 2002; 99: 3684-9.
69. Alexander K A, et al, M. Mungi. *Emerg Infect Dis* 2010; 16: 1296-9.
70. M Cristina G, et al. *PLoS Pathog* 2005; 1: 0055-61.
71. Delogu G, et al. *Infect Immun* 2001; 69: 5606-11.
72. Isom G L, et al. *Sci Rep* 2017; 7. DOI:10.1038/s41598-017-09111-6.
73. Newton-Foot M, et al. *BMC Evol Biol* 2016; 16. DOI:10.1186/s12862-016-0631-2.
74. Cooper T F, et al. *Proc Natl Acad Sci* 2000; 97: 12643-8.
75. Slayden R A, et al. Pathog. Dis. 2018; 76. DOI:10.1093/femspd/fty039.
76. Van Der Woude A D, et al. *J Biol Chem* 2012; 287: 20417-29.
77. Boritsch E C, et al. *Nat Microbiol* 2016; 1. DOI:10.1038/nmicrobiol.2015.19.
78. Cohen I, P et al. *Front Immunol* 2014; 5: 1-9.
79. Boritsch E C, S et al. *Mol. Microbiol.* 2014; 93: 835-52.
80. Houben E N G, et al. *Biochim Biophys Acta—Mol Cell Res* 2014; 1843: 1707-16.
81. Kumar S, et al. 2017: 3706-3706.
82 Bowdish D M E, Sakamoto K, Kim M J, et al. MARCO, TLR2, and CD14 are required for macrophage cytokine responses to mycobacterial trehalose dimycolate and *Mycobacterium tuberculosis*. *PLoS Pathog* 2009; 5. DOI: 10.1371/journal.ppat.1000474.
83. Fujita Y, et al. *Microbiology* 2005; 151: 3403-16.
84. Stavrum R, et al. *PLoS One* 2011; 6. DOI:10.1371/journal.pone.0026295.
85. Katoch V M. Infections due to non-tuberculous mycobacteria (NTM). Indian J. Med. Res. 2004; 120: 290-304.
86. Campbell I A, et al. *Eur Respir* 12003; 21: 478-82.
87. van Ingen J, et al. *Clin Infect Dis* 2008; 46: 1200-5.
88. Van Ingen J, et al. *Emerg Infect Dis* 2008; 14: 385-9.
89. Gey Van Pittius, et al. *BMC Evol Biol* 2006; 6. DOI: 10.1186/1471-2148-6-95.
90. Becq J, et al. *Mol Biol Evol* 2007; 24: 1861-71.
91. Jamwal S V, et al. *Sci Rep* 2016; 6. DOI:10.1038/srep23089.
92. Nguyen L. Arch. Toxicol. 2016; 90: 1585-604.
93. Lee J. et al. *Sci Rep* 2019; 9. DOI:10.1038/s41598-019-40814-0.
94. Roy S, et al. *Sci Rep* 2018; 8. DOI:10.1038/s41598-018-24509-6.

---

We claim:

1. A method of detecting *Mycobacterium riyadhense* (*M. riyadhense*) in a sample, the method comprising: contacting the sample with one or more primer pairs in a DNA amplification reaction,
    wherein *M. riyadhense* is detected after detecting the presence of an amplified product,
    wherein the amplified product has a size ranging from about 166 bp to about 994 bp, and
    wherein the primer pairs are selected from the group consisting of SEQ ID NOs: 1 and 2; SEQ ID Nos: 3 and 4; SEQ ID Nos: 5 and 6, SEQ ID Nos: 7 and 8; and variants thereof.

2. The method of claim 1, wherein the primer pair comprises SEQ ID NO:1 and SEQ ID NO:2 or variants thereof.

3. The method of claim 1, wherein the primer pair comprises SEQ ID NO:3 and SEQ ID NO:4 or variants thereof.

4. The method of claim 1, wherein the primer pair comprises SEQ ID NO:5 and SEQ ID NO:6 or variants thereof.

5. The method of claim 1, wherein the primer pair comprises SEQ ID NO:7 and SEQ ID NO:8 or variants thereof.

6. The method of claim 1, wherein the product is an amplified product of SEQ ID NO. 9, 10, 13 or 14, and/or, wherein the amplified product is about 994 bp, 511 bp, 372 bp or 166 bp in size.

7. The method of claim 1, wherein the method comprises amplifying SEQ ID NO:9 present in the sample.

8. The method of claim 1, wherein the method comprises amplifying SEQ ID NO:10 present in the sample.

9. The method of claim 1, wherein the method comprises amplifying SEQ ID NO:13 present in the sample.

10. The method of claim 1, wherein the method comprises amplifying SEQ ID NO:14 present in the sample.

11. The method of claim 7, wherein the amplified product has a size of about 372 bp.

12. The method of claim 8, wherein the amplified product has a size of about 994 bp.

13. The method of claim 9, wherein the amplified product has a size of about 166 bp.

14. The method of claim 10, wherein the amplified product has a size of about 511 bp.

15. The method of claim 1, wherein the sample is selected from the group consisting of sputum, breast milk, semen, bronchoalveolar lavage fluid, pleural fluid, urine, bronchial aspirate, pleural fluid, ascetic/peritoneal fluid, cerebrospinal fluid (CSF), pus, stool, amniotic fluid, menstrual blood, peripheral blood, other body fluids or aspirate, lymph node, and tissue biopsy.

16. The method of claim 1, further comprising a step of isolating DNA from the sample.

17. The method of claim 1, further comprising administering an antibiotic to a subject, providing the sample in which the presence of *M. riyadhense* is confirmed.

18. The method of claim 17, wherein the antibiotic is selected from the group consisting of rifampin, ethambutol, clarithromycin, rifabutin, linezolid, amikacin, moxifloxacin, ciproflaxacan, and trimethoprim-sulfamethoxazole.

19. The method of claim 1, wherein the amplification reaction employs a polymerase enzyme having 5' to 3' nuclease activity.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
ttcgttgtcg gtttcgtcgc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gcgtcagctc caccgaaaac                                              20

<210> SEQ ID NO 3
<211> LENGTH: 16
<212> TYPE: DNA
<213> ORGANISM: Artificial Sequence
<220> FEATURE:
<223> OTHER INFORMATION: Synthetic primer

<400> SEQUENCE: 3
ccaccgctgt tggcga                                                  16
```

```
<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
ttcgtcccgt tgatcccgtt                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
aacctgcccg atacgcactt                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
actgttcctc cgtggggttg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gactgtgggg taacggtgga                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ccggtgatgt cgcctactcc                                              20

<210> SEQ ID NO 9
<211> LENGTH: 909
<212> TYPE: DNA
<213> ORGANISM: Artificial Sequence
<220> FEATURE:
<223> OTHER INFORMATION: A gene sequence encoding MR_00036 hypothetical
      protein

<400> SEQUENCE: 9
gtgcgcccgg cgccgatccg ggtgcttcgt tgtcggtttc gtcgcgataa cgatgacggc    60
gtgggcgccg gtgttcttgc ggaggctcgg acgccggttc aggtgggggc gcggcgggtt   120
gcgcgggccc gccgatccgg acgcggcgcg gtaacggccc cggcggcgcc ggcggcgccg   180
gcggcgcttg cggcggtccg ttcgatggcg cggcggtgg cttgggcggt gctggcgggg   240
agctggcctt cggcgcatga gccgacggtc gttgcggcgc tgccaccgcg gcgcgcaccg   300
```

```
gcccgttgga tgttggcggt ggcggtggtt ggggaggggc ctgggggggt ccgccgattg        360
gcatcctcgg agtaccggtt ttcggtggag ctgacgctcg tggggacggg ggtggcggcg        420 tgggggggttg gggaggggcc tgcggccgtc cgccgatggg catgggggggt gccggtggtt       480 tgggcggagc acccgttggt tcggccgaag ccagtggcgg ttcgggtggc gcgggtggcg        540
gttcggccga agccagtggc ggttcgggtg gcgcgggtgg cggttcgggt ggcgcgggtg        600
gcggttcggg tggcgcgggt ggagttggcg gcggtccgcc gatgggcatg ggggggcgccg       660 gtggtttggg cccagctgcg gcgggcccgg cagttgcggt tgcggcggac ggccattcgg        720
gtggcgccgg cggttcgggc agcggcggcg gcggttcggg tgtgggcggc ggcggtgcgg        780
gtgtgggcgg cggcggtgcg ggtgtgggcg gcggcggtgc gggtgtgggc gattgcgccc        840
cgccgccgat tggcattgga gccggcggcg gttcgggtgg cgccggcgga ggctctaccg        900
gggacgtag                                                                909
```

<210> SEQ ID NO 10
<211> LENGTH: 1038
<212> TYPE: DNA
<213> ORGANISM: Artificial Sequence
<220> FEATURE:
<223> OTHER INFORMATION: A sequence encoding MR_00263 hypothetical
      protein <400> SEQUENCE: 10

```
ttgatcggca acggcggcgc cggcgggtcc ggtgccaccg ctgttggcga cggtaaggcc         60
ggcggtaacg gcgggcccgc cgggctgttc ggcaacggcg gggcaggcgg ggccggcggg        120
aactcactga gcggcaccgg cggggccggc ggccgtggcg gcgacgccat gctgttcggc        180
aacggcggcc ccggcggggc cggcgggtgg gcagggggca ctgcccaagt cgccggggcc        240
ggcggggccg gcggcaacgc cggttcgctc ttcggcgccg ccgggaccgg cggcgtcgga        300
gggtccgcca cagacaccgg cggtgacggc gggcccggcg gggccggcgg ggccggcggg        360
atgttcgcca gcggcggggc cggcggggcc ggcgggtctg gcggcaacac cgacggtgac        420
ggcggggccg gcggggccgg cggggccggc gggctgttcg gcgccggcgg tgacggcggg        480
gccggcgggg ctggcgggac caccgccacc ggcggggccg gcggggccgg gggcaacgcc        540
ggcatgctct cggtcggtgc cgccggcggc gccggcggca gcggcgggtc cggggacggt        600
atcggcggtg acggcggggc cggtgggacc ggcagcttaa tcttgggcgc cggcggcgcc        660
ggcggcgccg gcggcagcgg cgggaccacc gttagccccg gcatcggcgg ggccggcggg        720
gtaggtgggg ccggcggctt agtcataggc tctggcggca gcggcggcgc cggcgggttc        780
ggcaccatca ccggcggggc cggcggggcc ggcggcaagc ccggactgat tggcaatggc        840
ggtgacgggg gtaccggagg cgacggcggc atcggcggcg gcgccggtgg ggccggcggc        900
aacgccgtgc tgatcggcaa cggcggcaac ggcggcaacg gcggtggctt cgggcccgtc        960
aagggcaacg gcggcaccgg cggcaccggc gggctgctgc tcggcctgaa cgggatcaac       1020
gggacgaagg gcgtatag                                                     1038
```

<210> SEQ ID NO 11
<211> LENGTH: 25
<212> TYPE: DNA
<213> ORGANISM: Artificial Sequence
<220> FEATURE:
<223> OTHER INFORMATION: Synthetic primer
<400> SEQUENCE: 11

```
tggatccgac gaagtcgtaa caagg                                          25

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tggatagtgg ttgcgagcat                                                20

<210> SEQ ID NO 13
<211> LENGTH: 270
<212> TYPE: DNA
<213> ORGANISM: Artificial Sequence
<220> FEATURE:
<223> OTHER INFORMATION: A sequence encoding MR_00606 hypothetical
      protein

<400> SEQUENCE: 13
atgattgatt cgatgtcggc ggcgctgacc gccgtcaccc tgatcgagac cgccgtcggt    60
gcggacgacc gtctacagat cgcggccgcc ctcctgcccg acaacctgcc cgatacgcac   120
ttggtgctct caagcgcggt gtggtgcgcg caccacttgg ccgagtcgtt ggccgaggag   180
cttggcgtcg acatcgcaac cgtcaaggcg gcgctgcgcg acgaggtggc cgaacgattc   240
cagaactaca accccacgga ggaacagtga                                    270

<210> SEQ ID NO 14
<211> LENGTH: 789
<212> TYPE: DNA
<213> ORGANISM: Artificial Sequence
<220> FEATURE:
<223> OTHER INFORMATION: A sequence encoding MR_01005 hypothetical
      protein

<400> SEQUENCE: 14
gtggaccgac gcagcaaagc agccggcggg tcggccggac tgtggggtaa cggtggagca    60
ggcggcgccg gcggaacggg cacggccggg atcaatggcg gggccggcgg cgccggcggc   120
aacggcggac tgctctccgg cgccggcggg gccggcgccc acggcggtgc tggaattgcc   180
ggcgggccgg gcctggccgg aggtgccggc ggtgacggcg gagccggcgg caagggcggc   240
ctgtggatgg gccagggcgg cgcggccggg caaggaggtg acggcggcgc tggcggcgtc   300
ggcactaccg gtctgacggg cagcatcggc ggccaaggca gtaccggcgg caacggcggc   360
gcccgcggcg atagcggtgt cggcggcact aacggcagcg gcggccgtgg cggcgacggt   420
ggcatcggcg gcaccggcgg caccggcggc accggcggcc cggcaccac aactatggcc   480 gggggaccg gcggcaacgg cggcgacggc ggcaacggtg gtgcaaacgg agtaggcgac   540
atcaccggca tccctgtcgc tggctccgac ggtgtcggcg gcgacggcgg cttcggcggc   600
gacggcggcg acggcggcac tacaggcggc gtcggcgcga gcggtggcgc gggcggcaac   660
ggcggtgccg gcgacggagg agcggctggc accggctcac ccggcacccc cggcacgccg   720
aacgcgggta cctcgggcgg cgacggcggg accggagggg cgggtggctc tggtgggggg   780
cccacatag                                                          789
```